(12) United States Patent
Nakazato et al.

(10) Patent No.: US 6,600,038 B1
(45) Date of Patent: Jul. 29, 2003

(54) CARBAMOYL TETRAHYDROPYRIDINE DERIVATIVES

(75) Inventors: Atsuro Nakazato, Tokyo (JP);
Taketoshi Okubo, Tokyo (JP);
Toshihito Kumagai, Tokyo (JP);
Kazuyuki Tomisawa, Tokyo (JP)

(73) Assignee: Taisho Pharmaceutical Co., Ltd. (JP)

( * ) Notice: Subject to any disclaimer, the term of this patent is extended or adjusted under 35 U.S.C. 154(b) by 0 days.

(21) Appl. No.: 09/914,534

(22) PCT Filed: Mar. 10, 2000

(86) PCT No.: PCT/JP00/01468

§ 371 (c)(1),
(2), (4) Date: Aug. 30, 2001

(87) PCT Pub. No.: WO00/53604

PCT Pub. Date: Sep. 14, 2000

(30) Foreign Application Priority Data

Mar. 11, 1999 (JP) .......................... 11-065004
Jun. 30, 1999 (JP) .......................... 11-185628
Sep. 13, 1999 (JP) .......................... 11-258353

(51) Int. Cl.$^7$ ................... C07D 473/34; C07D 487/04; C07D 207/34; C07D 211/78
(52) U.S. Cl. .................. 544/61; 544/117; 544/118; 544/254; 544/262; 544/265; 544/277; 544/280
(58) Field of Search ................. 544/280, 262, 544/265, 277, 254, 117, 118, 61

(56) References Cited

U.S. PATENT DOCUMENTS 4,229,453 A    10/1980    Roth et al. ................... 424/251

FOREIGN PATENT DOCUMENTS

| EP | 0 976 745 A1 | 3/1998 |
| JP | 11-335376 | 12/1999 |
| JP | 2000-86663 | 3/2000 |
| WO | 94/13676 | 6/1994 |

OTHER PUBLICATIONS

Biochemical Pharmacology, vol. 37, No. 19, pp. 3749–3753, 1988.
Tetrahedron Letters, vol. 26, No. 9, pp. 1229–1232, 1985.

*Primary Examiner*—Mark L. Berch
*Assistant Examiner*—Kahsay Habte
(74) *Attorney, Agent, or Firm*—Lorusso, Loud & Kelly

(57) ABSTRACT

Carbamoyl tetrahydropyridine derivatives represented by the formula:

[in the formula, $R^1$ and $R^2$ are identical or different, and each represents a hydrogen atom, a $C_1$–$C_5$ alkyl group, or the like; $Y^1$–$Y^2$ represents $(R^4)C$=$C(R^5)$, $(R^6)C$=N, N=N, $(R^7)$N—CO, or N=$C(R^8)$; $X^1$, $X^2$, and $X^3$ are identical or different, and each represents a hydrogen atom, a halogen atom, or the like; $R^3$, $R^4$, $R^5$, and $R^6$ are identical or different, and each represents a hydrogen atom or an alkyl group; $R^7$ represents a hydrogen atom, a $C_1$–$C_5$ alkyl group, or the like; and $R^8$ represents a hydrogen atom or a carbamoyl group] or a pharmaceutically acceptable salt thereof, and intermediates for the preparation thereof are provided.

The derivatives described above are effective for diseases which are believed to involve CRF.

7 Claims, No Drawings

CARBAMOYL TETRAHYDROPYRIDINE DERIVATIVES

FIELD OF TECHNOLOGY

The present invention relates to therapeutic agents for diseases involving Corticotropin Releasing Factor (CRF), such as depression, anxiety, Alzheimer's disease, Parkinson's disease, Huntington's chorea, eating disorders, hypertension, digestive tract diseases, drug dependence, cerebral infarction, cerebral ischemia, cerebral edema, head trauma, inflammation, and immune system-related diseases.

BACKGROUND ART

CRF is a hormone comprising 41 amino acids (Science, 213, 1394–1397, 1981; and J. Neurosci., 7, 88–100, 1987) and it is suggested that CRF plays central roles in bioreactions in stress (Cell. Mol. Neurobiol., 14, 579–588, 1994; Endocrinol., 132, 723–728, 1994; and Neuroendocrinol. 61, 445–452, 1995). CRF acts in two pathways: one acting on the peripheral immune system and sympathetic nervous system via the hypothalamus-pituitary-adrenal system, and another in which it acts as a neurotransmitter in the central nervous system (in Corticotropin Releasing Factor: Basic and Clinical Studies of a Neuropeptide, pp 29–52, 1990). In the case where CRF is intraventricularly administered to hypophysectomized rats and to normal rats, symptoms of anxiety occur in both rats (Pharmacol. Rev., 43, 425–473, 1991; and Brain Res. Rev., 15, 71–100, 1990). Therefore, it is believed that CRF is involved in the hypothalamus-pituitary-adrenal system and that CRF functions as a neurotransmitter in the central nervous system.

The diseases in which CRF is involved are summarized in a review by Owens and Nemeroff in 1991 (Pharmacol. Rev., 43, 425–474, 1991). Namely, CRF is involved in depression, anxiety, Alzheimer's disease, Parkinson's disease, Huntington's chorea, eating disorder, hypertension, digestive tract diseases, drug dependence, inflammation, immune system-related diseases, and the like. Recently, it is reported that CRF is also involved in epilepsy, cerebral infarction, cerebral ischemia, cerebral edema, and head trauma (Brain Res. 545, 339–342, 1991; Ann. Neurol. 31, 48–498, 1992; Dev. Brain Res. 91, 245–251, 1996; and Brain Res. 744, 166–170, 1997), and for this reason, CRF-receptor antagonists are useful as therapeutic agents for these diseases.

An objective of the present invention is to provide CRF antagonists effective on therapeutic agents or prophylactic agents for the diseases, which CRF participates in, such as depression, anxiety, Alzheimer's disease, Parkinson's disease, Huntington's chorea, eating disorder, hypertension, digestive apparatus disease, drug dependence, epilepsy, cerebral infarction, cerebral ischemia, cerebral edema, head trauma, inflammation, and immune system-related diseases.

DISCLOSURE OF THE INVENTION

As a result of diligent research with regard to carbamoyl tetrahydropyridine derivatives, the present inventors discovered novel carbamoyl tetrahydropyridine derivatives which exhibit high affinity for CRF receptors, and in addition, pyrrolopyrimidine derivatives, pyrrole derivatives, and carbamoyl-1,2,3,6-tetrahydropyridines which are intermediates necessary for synthesizing said novel carbamoyl tetrahydropyridine derivatives, consequently completed the present invention.

In the following, the present invention is explained.

The present invention corresponds to a carbamoyl tetrahydropyridine derivative represented by Formula [1] as follows:

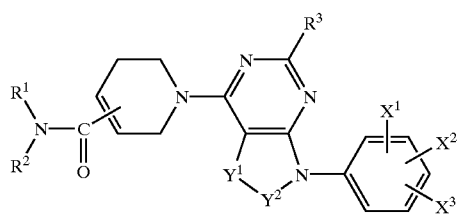

[in the formula, $R^1$ and $R^2$ are identical or different, and each represents a hydrogen atom, a $C_1$–$C_5$ alkyl group, or a phenyl group, or alternatively, $R^1$ and $R^2$, taken together with the nitrogen atom to which they are adjacent, represent a 5- to 8-membered and saturated heterocyclic group represented by the formula:

(in the formula, A represents $CH_2$, NH, N—($C_1$–$C_5$ alkyl), O or S); $R^3$ represents a hydrogen atom or a $C_1$–$C_5$ alkyl group; $Y^1$–$Y^2$ represents $(R^4)C=C(R^5)$, $(R^6)C=N$, $N=N$, $(R^7)N$—CO, or $N=C(R^8)$; $X^1$, $X^2$, and $X^3$ are identical or different, and each represents a hydrogen atom, a halogen atom, a $C_1$–$C_5$ alkyl group, a $C_1$–$C_5$ alkoxy group, a $C_1$–$C_5$ alkylthio group, a tuifluoromethyl group, a trifluoromethoxy group, an amino group, or a $C_1$–$C_5$ alkylamino group; wherein $R^4$ and $R^5$ are identical or different, and each represents a hydrogen atom or a $C_1$–$C_5$ alkyl group; $R^6$ represents a hydrogen atom or a $C_1$–$C_5$ alkyl group; $R^7$ represents a hydrogen atom, a $C_1$–$C_5$ alkyl group, a ($C_1$–$C_5$ alkoxy)carbonylmethyl group, a carboxymethyl group, or a group represented by the formula: $CH_2CONR^{11}(R^{12})$ (in the formula, $R^{11}$ and $R^{12}$ are identical or different, and each represents a hydrogen atom or a $C_1$–$C_5$ alkyl group, or alternatively, $R^{11}$ and $R^{12}$, taken together with the nitrogen atom to which they are adjacent, represent a 5- to 8-membered and saturated heterocyclic group represented by the formula:

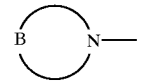

(in the formula, B represents $CH_2$, NH, N—($C_1$–$C_5$ alkyl), O or S; and $R^8$ represents a hydrogen atom or a carbamoyl group], or a pharmaceutically acceptable salt thereof. Among these, the compounds wherein $R^1$ and $R^2$ represent a hydrogen atom are preferable, and the compounds wherein $R^3$ represents a methyl group; $Y^1$–$Y^2$ represents $(R^4)C=C(R^5)$; and $R^4$ and $R^5$ are identical or different, and each represents a hydrogen atom or a methyl group are more preferable.

In addition, another present invention corresponds to a pyrrolopyrimidine derivative represented by Formula [2] as follows:

[2]

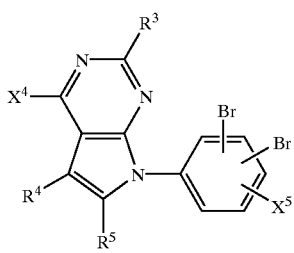

(in the formula $R^3$ represents a hydrogen atom or a $C_1$–$C_5$ alkyl group; $R^4$ and $R^5$ are identical or different, and each represents a hydrogen atom or a $C_1$–$C_5$ alkyl group; $X^4$ represents a hydroxyl group, a chlorine atom, a bromine atom, or an iodine atom; and $X^5$ represents a halogen atom, a $C_1$–$C_5$ alkyl group, a $C_1$–$C_5$ alkoxy group, a $C_1$–$C_5$ alkylthio group, a trifluoromethyl group, or a trifluoromethoxy group).

Furthermore, another present invention corresponds to a pyrrole derivative represented by Formula [3] as follows:

[3]

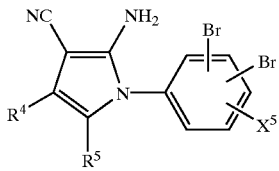

(in the formula, $R^4$ and $R^5$ are identical or different, and each represents a hydrogen atom or a $C_1$–$C_5$ alkyl group; and $X^5$ represents a halogen atom, a $C_1$–$C_5$ alkyl group, a $C_1$–$C_5$ alkoxy group, a $C_1$–$C_5$ alkylthio group, a trifluoromethyl group, or a trifluoromethoxy group).

In addition, another present invention corresponds to a 4- or 5-carbamoyl-1,2,3,6-tetrahydropyridine represented by Formula [4] as follows:

[4]

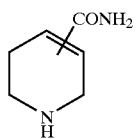

or a pharmaceutically acceptable salt thereof.

In Formula [1] of the present invention, the substituent position of the $(R^2)R^1NCO$ group is present at the 4-position or the 5-position.

In addition, the terms used in the present invention are defined as follows.

The $C_1$–$C_5$ alkyl group means a straight-chain or branched-chain alkyl group having 1 to 5 carbon atoms. As an example thereof, mention may be made of a methyl group, an ethyl group, a propyl group, an isopropyl group, a butyl group, an isobutyl group, a tert-butyl group, a cyclopropylmethyl group, a pentyl group, an isopentyl group, or the like.

The saturated heterocyclic group means a 5- to 8-membered and saturated heterocyclic group which may include a nitrogen atom, an oxygen atom, or a sulfur atom as an atom for forming the ring, while it is not particularly restricted since any saturated heterocyclic groups capable of providing the compounds represented by Formula (10) shown in the reaction scheme described below may be synthesized. Examples thereof include a pyrrolidino group, a piperidino group, a morpholino group, a thiomorpholino group, a piperazino group, a 4-methylpiperazino group, and the like.

The halogen atom denotes a fluorine atom, a chlorine atom, a bromine atom, or an iodine atom.

The $C_1$–$C_5$ alkoxy group means a straight-chain or branched-chain alkoxy group having 1 to 5 carbon atoms. As an example thereof, mention may be made of a methoxy group, an ethoxy group, a propoxy group, an isopropoxy group, a butoxy group, an isobutoxy group, a pentyloxy group, an isopentyloxy group, or the like.

The $C_1$–$C_5$ alkylthio group means a straight-chain or branched-chain alkylthio group having 1 to 5 carbon atoms. As an example thereof, mention may be made of a methylthio group, an ethylthio group, a propylthio group, an isopropylthio group, a butylthio group, an isobutylthio group, a pentylthio group, an isopentylthio group, or the like.

The $C_1$–$C_5$ alkylamino group means an amino group which is substituted with one or two straight-chain or branched-chain alkyl groups having 1 to 5 carbon atoms. As an example thereof, mention may be made of a methylamino group, a dimethylamino group, an ethylamino group, a diethylamino group, a propylamino group, a dipropylamino group, an isopropylamino group, or the like.

The ($C_1$–$C_5$ alkoxy)carbonylmethyl group means a carbonylmethyl group which is substituted with a straight-chain or branched-chain alkoxy group having 1 to 5 carbon atoms. As an example thereof, mention may be made of a methoxycarbonylmethyl group, an ethoxycarbonylmethyl group, a propoxycarbonylmethyl group, an isopropoxycarbonylmethyl group, a butoxycarbonylmethyl group, an isobutoxycarbonylmethyl group, a pentyloxycarbonylmethyl group, an isopentyloxycarbonylmethyl group, or the like.

As an example of the groups represented by the formula: $CH_2CONR^{11}(R^{12})$, mention may be made of, for example, a carbamoylmethyl group, an N-methylcarbamoylmethyl group, an N,N-dimethylcarbamoylmethyl group, an N-ethylcarbamoylmethyl group, an N,N-diethylcarbamoylmethyl group, an N-propylcarbamoylmethyl group, an N,N-dipropylcarbamoylmethyl group, an N-isopropylcarbamoylmethyl group, a pyrrolidinocarbonylmethyl group, a piperidinocarbonylmethyl group, a morpholinocarbonylmethyl group, a piperazinocarbonylmethyl group, or the like.

In addition, the pharmaceutically acceptable salt in the present invention refers to, for example, a salt with an inorganic acid such as sulfuric acid, hydrochloric acid, or phosphoric acid; a salt with an organic acid such as acetic acid, oxalic acid, lactic acid, tartearic acid, fumaric acid, maleic acid, citric acid, benzenesulfonic acid, or methanesulfonic acid; or the like.

The compounds represented by Formulae [1], [2], [3], and [4] may be prepared as follows:

(in the following reaction schemes, $R^1$, $R^2$, $R^3$, $R^4$, $R^5$, $R^6$, $R^7$, $R^8$, $Y^1$–$Y^2$, $X^1$, $X^2$, $X^3$, $X^4$, and $X^5$ have the same meanings as described above; $R^9$ and $R^{10}$ are identical or different, each represents a $C_1$–$C_5$ alkyl group or a benzyl group; $R^{13}$ represents a $C_1$–$C_5$ alkyl group; Boc represents a tert-butoxycarbonyl group; and $X^6$ repre sents a chlorine atom, a bromine atom, an iodine atom, a methanesulfonyloxy group, a benzensulfonyloxy group, a toluenesulfonyloxy group, or a trifluoromethanesulfonyloxy group).

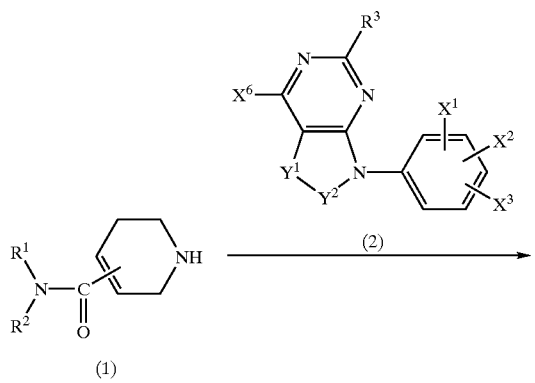

(1) + (2) → (3)

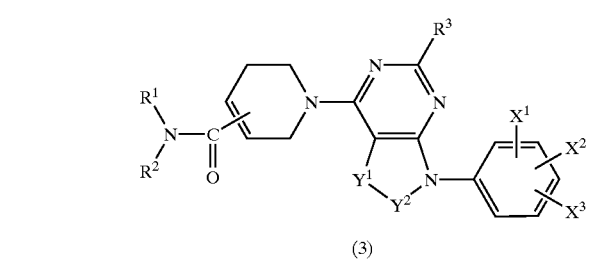

A carbamoyltetrahydropyridine derivative (3) which corresponds to the compound of the present invention can be prepared by reacting a 4- or 5-carbamoyl-1,2,3,6-tetrahydropyridine derivative (1) with a compound (2) in the presence or absence of a base, in an inert solvent.

Herein, as examples of the base, mention may be made of, for example, organic bases such as triethylamine, diisopropylethylamine, or pyridine; inorganic bases such as sodium carbonate, potassium carbonate, sodium hydrogencarbonate, potassium hydrogencarbonate, sodium hydroxide, or sodium hydride; alcoholates such as sodium methoxide, sodium ethoxide, or potassium tert-butoxide; metal amides such as sodium amide, or lithium diisopropylamide; or Grignard reagents such as methyl magnesium bromide; or the like. As examples of the inert solvent, mention may be made of, for example, alcohols such as methanol, ethanol, isopropyl alcohol, or ethylene glycol; ethers such as diethyl ether, tetrahydrofuran, dioxane, or 1,2-dimethoxyethane; hydrocarbons such as benzene or toluene; amides such as N,N-dimethylformamide; acetonitrile; water; mixed solvents selected from these solvents; or the like.

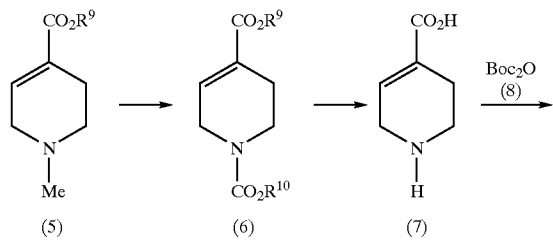

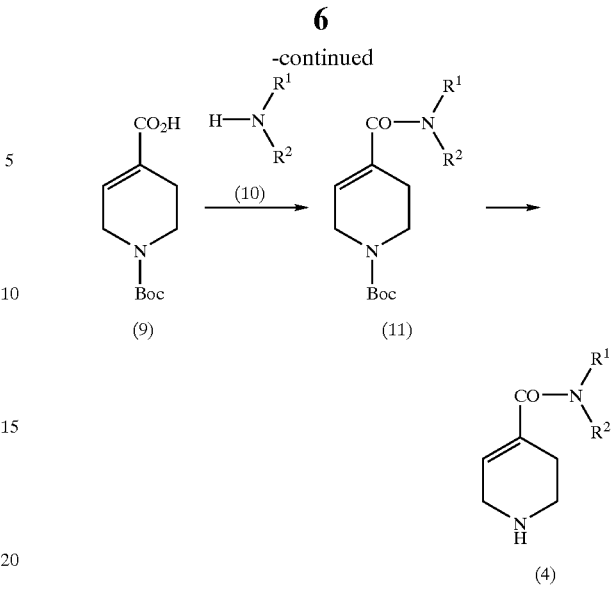

A 4-carbamoyl-1,2,3,6-tetrahydropyridine derivative (4) can be prepared by a sequence of operations of N-protection on a 1,2,3,6-tetrahydropyridine-4-carboxylic acid (7), amidation, and deprotection of N-Boc. The 1,2,3,6-tetrahydropyridine-4-carboxylic acid (7) may be synthesized by conversion of the methyl group of a N-methyl-4-alkoxycarbonyl-1,2,3,6-tetrahydropyridine (5), followed by a hydrolysis.

Herein, the conversion of the methyl group means to replace the N-methyl group with an alkoxycarbonyl group, and for example, to react with haloformates such as ethyl chloroformate or benzyl chloroformate in the presence or absence of an organic base such as diisopropylethylamine or an inorganic base such as potassium carbonate in an inert solvent such as benzene, toluene, chloroform, or the like. The hydrolysis means elimination of an N-substituent of a compound (6) and hydrolysis of an ester group, and for example, means to react under an acidic condition such as with hydrobromic acid or a basic condition such as with barium hydroxide. The N-protection means to protect the NH group of the compound (7) with a tert-butoxycarbonyl group (Boc), and for example, N-Boc protection can be conducted by the common methods using $(Boc)_2O$ or the like. The amidation refers to, for example, an amidation via an acid halide such as an acid chloride or an acid bromide, an amidation via an anhydride of a mixed acid using haloformates such as ethyl chloroformate, isobutyl chloroformate, or a common amidation: using a condensing agent such as 1-(3,3-dimethylaminopropyl)-3-ethylcarbodiimide, 1,3-dicyclohexylcarbodiimide, diphehylphosphorylazide, diethyl cyanophosphate, or carbonyldiimidazole. Deprotection of N-Boc refers to a general reaction for removing a Boc group, and for example, refers to reacting, for example, trifluoroacetic acid, hydrogen chloride, formic acid, or the like in an inert solvent such as ethyl acetate, dichloromethane, chloroform, dioxane, water or the like. With regard to the hydrolysis of the ester, N-protection, and deprotection of N-Boc, the methods as described in PROTECTIVE GROUPS IN ORGANIC SYNTHESIS, written by THEODORA W. GREENE and PETER G. M. WUTS may be employed.

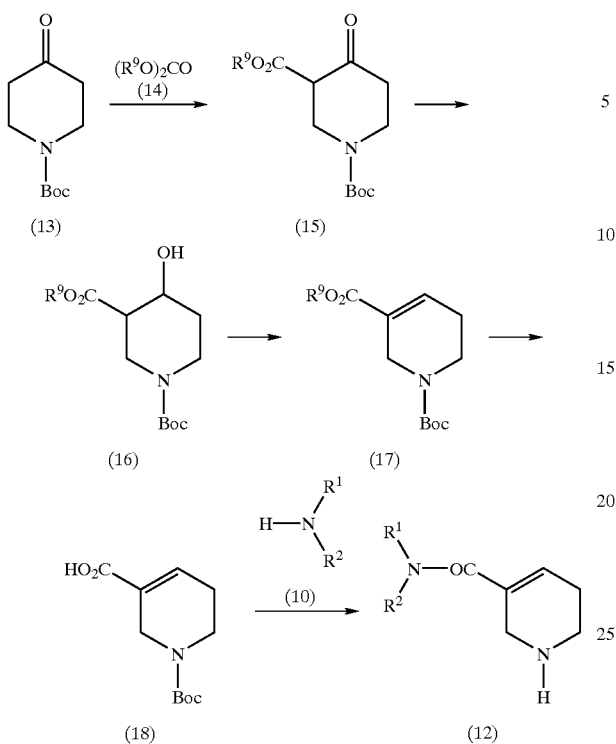

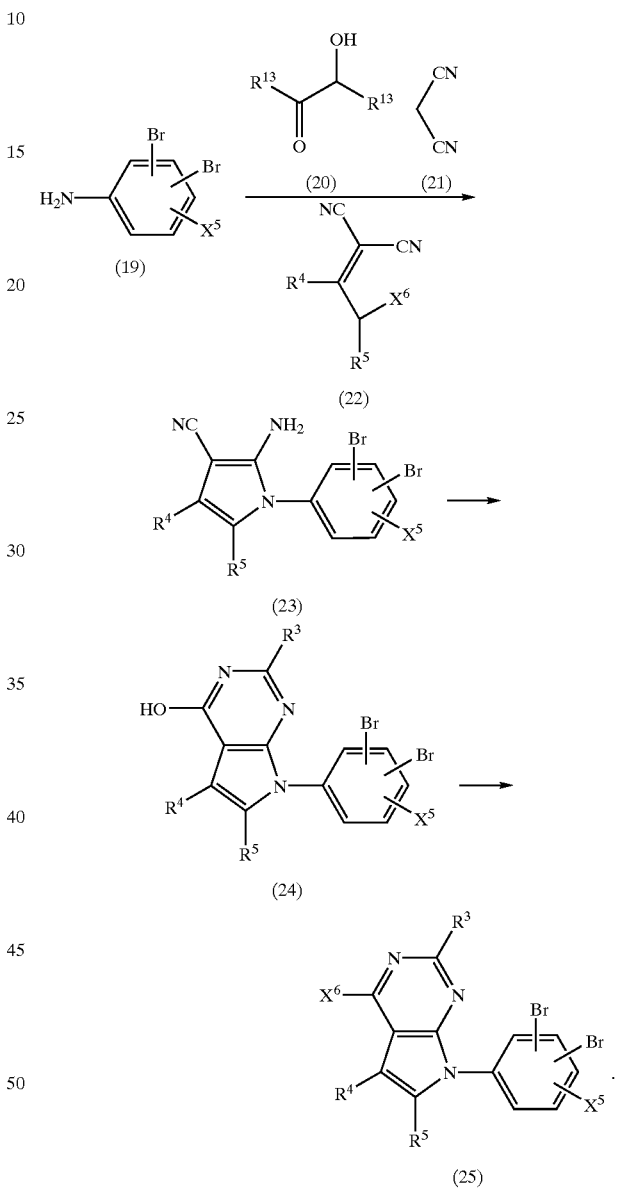

A 5-carbamoyl-1,2,3,6-tetrahydropyridine derivative (12) can be prepared from an N-Boc-1,2,3,6-tetrahydropyridine-5-carboxylic acid (18), in the same manner as that of the synthesis method of said 4-carbamoyl-1,2,3,6-tetrahydropyridine derivative (4) from said N-Boc-1,2,3,6-tetrahydropyridine-4-carboxylic acid (9). The N-Boc-1,2,3,6-tetrahydropyridine-5-carboxylic acid (18) can be derived by a condensation reaction of an N-Boc-4-piperidone (13) with a dialkyl carbonate, reduction, and elimination of the hydroxyl group, followed by a hydrolysis.

Herein, the condensation with a dialkyl carbonate refers to reacting with the dialkyl carbonates such as dimethyl carbonate or diethyl carbonate in the presence of a base, examples of which include, for example, inorganic bases such as sodium hydride or potassium hydride; alcoholates such as sodium methoxide, sodium ethoxide, or potassium tert-butoxide; metal amides such as sodium amide or lithium diisopropylamide; or the like, in an inert solvent, examples of which include, for example, alcohols such as methanol, ethanol, isopropyl alcohol, or ethylene glycol; ethers such as diethyl ether, tetrahydrofuran, dioxane, or 1,2-dimethoxyethane; hydrocarbons such as benzene or toluene; amides such as N,N-dimethylformamide; or the like. The reduction refers to a reduction of common ketones to alcohols, and for example, refers to a reduction by inorganic reductants such as sodium borohydride; a reduction by hydrogenation using palladium/carbon, platinum oxide, or the like; or the like. The elimination of the hydroxyl group refers to converting the hydroxyl group of the compound (16) into a leaving group followed by a reaction, and refers to, for example, a halogenation by thionyl chloride, triphenylphosphine-carbon tetrabromide, or the like; an acylation, for example, by acetyl chloride, or the like; or a sulfonylation, for example, by methanesulfonyl chloride, benzenesulfonyl chloride, toluenesulfonyl chloride, or trifluoromethanesulfonic anhydride, followed by an elimination reaction by a base treatment with, for example 1,8-diazabicyclo[5.4.0]-7-undecene, pyridine, or the like. The hydrolysis refers to a common hydrolysis of esters, and for example, refers to reacting using a base such as sodium hydroxide or potassium hydroxide in an inert solvent such as alcohol, water, or the like. With regard to the hydrolysis of the ester, the methods as described in PROTECTIVE GROUPS IN ORGANIC SYNTHESIS, written by THEODORA W. GREENE and PETER G. M. WUTS may be employed.

A pyrrole derivative (23), which is a compound of the present invention, can be prepared by reacting an aniline derivative (19) and a compound (20) in the presence of organic acids, inorganic acids, or Lewis acids, such as p-toluene sulfonic acid, hydrogen chloride, zinc chloride, or the like, under azeotropic dehydration conditions in a solvent of hydrocarbons such as toluene, adding malononitrile (21) to this reaction mixture, and reacting the mixture, under azeotropic dehydration conditions, or while the solvent is being removed by heating to 150 to 250° C. Alternatively, the pyrrole derivative (23) can also be prepared by reacting the aniline derivative (19) and an ethylidene malononitrile derivative (22) in the presence or absence of a base in the presence or absence of an inert solvent at a reaction temperature ranging from room temperature to 250° C. Herein, as examples of the inert solvent, mention may be made of, for example, alcohols such as ethanol or isopropyl alcohol; hydrocarbons such as toluene or benzene; ethers such as tetrahydrofuran or 1,2-dimethoxyethane; or the like. Examples of the base include, for example, inorganic bases such as sodium hydride or potassium carbonate or organic bases such as pyridine, N-methylmorpholine, or triethylamine.

In addition, the pyrrole derivative (23) is reacted with an acid anhydride such as acetic anhydride in an inert solvent such as acetic acid at a temperature ranging from an ice-cooled temperature to 150° C., and subsequently, a treatment is carried out using inorganic acids such as phosphoric acid at a temperature ranging from an ice-cooled temperature to 150° C., thereby a pyrrolopyrimidine derivative (24) which is the compound of the present invention can be obtained.

In addition, the pyrrolopyrimidine derivative (24) is reacted with a halogenating agent such as phosphorus oxychloride at a temperature ranging from room temperature to 150° C., thereby a derivative (25) which is the compound of the present invention can be derived.

The compounds of the present invention are useful as therapeutic agents or prophylactic agents for diseases which are considered to involve CRF. For this purpose, the compounds of the present invention may be formulated into tablets, pills, capsules, granules, powders, liquids, emulsions, suspensions, injections, or the like, according to the conventional formulation methods, by adding fillers, binders, disintegrants, pH regulators, solubilizers, and the like, which are in common use.

The compounds of the present invention may be administered orally or parenterally to an adult patient in a quantity of 0.1 to 500 mg per day in a single dose or divided doses. The dose can be increased or decreased as appropriate in consideration of the type of disease being treated, and the age, weight, and symptoms of each individual patient.

BEST MODES FOR CARRYING OUT THE INVENTION

In the following, the present invention is illustrated in detail by describing Examples and an Experimental Example.

EXAMPLE 1

Synthesis of 4-(4-Carbamoyl-1,2,3,6-tetrahydropyridin-1-yl)-2,5-dimethyl-7-(4-isopropyl-2-methylthiophenyl)-7H-pyrrolo[2,3-d]pyrimidine 1) In 640 ml of benzene, 108.9 g of ethyl 1-methyl-1,2,3,6-tetrahydropyridine-4-carboxylate and 41.6 g of diisopropylethylamine were dissolved, and subsequently, 279.1 g of ethyl chloroformate was added dropwise thereto over 70 minutes. The reaction mixture was heated under reflux for 30 minutes, followed by cooling the reaction mixture to room temperature. A saturated aqueous solution of sodium hydrogencarbonate was poured thereinto. After the reaction mixture was extracted with ethyl acetate, the extract was washed with saturated brine and was then dried over anhydrous sodium sulfate. The desiccant was filtered off, and the filtrate was concentrated under reduced pressure. The residue was purified by silica gel column chromatography (eluent:hexane-ethyl acetate=7:1) to yield 104.4 g of ethyl 1-ethoxycarbonyl-1,2,3,6-tetrahydropyridine-4-carboxylate as an oil.

2) To 104.4 g of ethyl 1-ethoxycarbonyl-1,2,3,6-tetrahydropyridine-4-carboxylate, 1500 g of 47% hydrobromic acid was added, and the mixture was heated under reflux for 100 hours. The reaction mixture was concentrated under reduced pressure to yield crude 1,2,3,6-tetrahydropyridine-4-carboxylic acid hydrobromide. The obtained crude 1,2,3,6-tetrahydropyridine-4-carboxylic acid hydrobromide was dissolved in a mixed solution of 0.48 l of dioxane and 0.48 l of a 2M aqueous solution of sodium hydroxide, and 105.2 g of tert-butyl bicarbonate were added thereto. The reaction mixture was stirred overnight at room temperature. The reaction mixture was concentrated under reduced pressure, and 1.4 l of a 1M aqueous solution of potassium hydrogensulfate was poured thereinto. The precipitated crystals of 1-tert-butoxycarbonyl-1,2,3,6-tetrahydropyridine-4-carboxylic acid was obtained in an amount of 100.5 g by filtration.

3) In a mixed solution of 400 ml of chloroform and 100 ml of dimethylformamide, 20.0 g of 1-tert-butoxycarbonyl-1,2,3,6-tetrahydropyridine-4-carboxylic acid was dissolved, and 14.2 g of 1-hydroxybenzotriazole hydrate and 17.7 g of 1-(3-dimethylaminopropyl)-3-ethylcarbodiimide hydrochloride were added thereto. The reaction mixture was stirred for 40 minutes at room temperature. The reaction solution was ice-cooled, and subsequently, 5.6 ml of 28% aqueous ammonia was added thereto, followed by stirring for 6 hours. The reaction mixture was warmed up to room temperature, and was concentrated under reduced pressure. A 5% aqueous solution of potassium hydrogensulfate was poured thereinto. The reaction mixture was extracted with ethyl acetate. The extract was washed with a saturated aqueous solution of sodium hydrogencarbonate and saturated brines, and was then dried over anhydrous sodium sulfate. After the desiccant was filtered off, the filtrate was concentrated under reduced pressure. The residue was purified by silica gel column chromatography (eluent:hexane-ethyl acetate=1:2) to yield 5.1 g of 1-tert-butoxycarbonyl-4-carbamoyl-1,2,3,6-tetrahydropyridine as a crystal.

4) In 20 ml of chloroform, 3.7 g of 1-tert-butoxycarbonyl-4-carbamoyl-1,2,3,6-tetrahydropyridine was dissolved, and 13 ml of trifluoroacetic acid were added thereto. The reaction mixture was stirred for 1 hour at room temperature, and subsequently was concentrated under reduced pressure to yield 4.1 g of crude 4-carbamoyl-1,12,3,6-tetrahydropyridine trifluoroacetate as a crystal.

The crude 4-carbamoyl-1,2,3,6-tetrahydropyridine trifluoroacetate was dissolved in ethyl acetate, and hydrogen chloride was bubbled thereinto, followed by concentration under reduced pressure to yield crystals of 4-carbamoyl-1,2,3,6-tetrahydropyridine hydrochloride.

m.p. 243–245° C.

4-carbamoyl-1,2,3,6-tetrahydropyridine hydrochloride was dissolved in a saturated aqueous solution of sodium hydrogen carbonate, followed by extraction with chloroform. The organic layer was dried over anhydrous sodium sulfate. After the desiccant was filtered off, the filtrate was concentrated under reduced pressure to yield crystals of free 4-carbamoyl-1,2,3,6-tetrahydropyridine.

m.p. 104–106° C.

5) In 4 ml of ethanol, 0.25 g of 4-carbamoyl-1,2,3,6-tetrahydropyridine trifluoroacetate and 0.35 g of 4-chloro-2,5-dimethyl-7-(isopropyl-2-methylthiophenyl)-7H-pyrrolo[2,3-d]pyrimidine were dissolved, and 0.39 g of diisopropylethylamine were added thereto. The reaction mixture was heated under reflux for 7.5 hours, and subsequently, a saturated aqueous solution of sodium hydrogencarbonate was poured into the reaction mixture. The reaction mixture was extracted with ethyl acetate. The extract was washed with saturated brine, and subsequently dried over anhydrous sodium sulfate. After the desiccant was filtered off, the filtrate was concentrated under reduced pressure. The residue was purified by silica gel column chromatography (eluent: chloroform—methanol=60:1), followed by crystallization from a mixed solvent of ethyl acetate-diethyl ether to yield 0.17 g of 4-(4-carbamoyl-1,2,3,6-tetrahydropyridin-1-yl)-2,5-dimethyl-7-(4-isopropyl-2-methylthiophenyl)-7H-pyrrolo [2,3-d]pyrimidine.

The structures and physical data of the present compound and of the compounds obtained in the, same manner as described above are shown in Table 1.

EXAMPLE 2

Synthesis of 4-(5-Carbamoyl-1,2,3,6-tetrahydropyridin-1-yl)-7-(4-isopropyl-2-methylthiophenyl)-2,5,6-trimethyl-7H-pyrrolo[2,3-d]pyrimidine 1) Sodium hydride in an oil in an amount of 6.2 g was washed with hexane twice and was subsequently suspended in 30 ml of tetrahydrofuran. A small amount of potassium hydride in an oil and 14.8 g of diethyl carbonate were added thereto. While the reaction mixture was heated under reflux, a solution of 10.0 g of 1-tert-butoxycarbonyl-4-piperidone dissolved in tetrahydrofuran was added dropwise thereto over 10 minutes. The reaction mixture was further heated under reflux for 5.5 hours, and subsequently, the reaction mixture was ice-cooled. A 0.8M aqueous solution of potassium hydrogensulfate in an amount of 200 ml was poured thereinto. The reaction mixture was extracted with ethyl acetate. The extract was washed with saturated brine, and was then dried over anhydrous sodium sulfate. After the desiccant was filtered off, the filtrate was concentrated under reduced pressure. The residue was purified by silica gel column chromatography (eluent:hexane-ethyl acetate≦15:1 to 4:1) to yield 11.9 g of 1-tert-butoxycarbonyl-3-ethoxycarbonyl-4-piperidone as a crystal.

2) In 60 ml of ethanol, 6.1 g of 1-tert-butoxycarbonyl-3-ethoxycarbonyl-4-piperidone was dissolved, and subsequently, 100 mg of platinum oxide was added thereto, followed by stirring for 2 hours at room temperature under a hydrogen atmosphere. After the platinum oxide was filtered off using celite, the filtrate was concentrated under reduced pressure to yield crude 1-tert-butoxycarbonyl-3-ethoxycarbonyl-4-hydroxypiperidine. The obtained crude 1-tert-butoxycarbonyl-3-ethoxycarbonyl-4-hydroxypiperidine was dissolved in 100 ml of chloroform, and subsequently, 11.4 g of triethylamine and 0.55 g of 4-dimethylaminopyridine were added thereto. Methanesulfonyl chloride in an amount of 6.2 g was added dropwise thereto with ice-cooling. The reaction mixture was stirred for 5.5 hours at room temperature. The reaction mixture was washed successively with a saturated aqueous solution of sodium hydrogencarbonate and saturated brine, and subsequently, was dried over anhydrous sodium sulfate. After the desiccant was filtered off, the filtrate was concentrated under reduced pressure to yield crude 1-tert-butoxycarbonyl-3-ethoxycarbohylpiperidin-4-yl methanesulfonate. The obtained crude 1-tert-butoxycarbonyl-3-ethoxycarnonylpiperidin-4-yl methanesulfonate was dissolved in 50 ml of benzene, and 3.4 g of 1,8-diazabicyclo [5.4.0]-7-undecene was added thereto, followed by heating under reflux for 30 minutes. After the reaction mixture was cooled to room temperature, it was washed with a 5% aqueous solution of potassium hydrogensulfate and saturated brine, and was then dried over anhydrous sodium sulfate. After the desiccant was filtered off, the filtrate was concentrated under reduced pressure. The residue was purified by silica gel column chromatography (eluent:hexane-ethyl acetate=10:1 to 6:1) to yield 5.3 g of 1-tert-butoxycarbonyl-5-ethoxycarbonyl-1,2,3,6-tetrahydropyridine as an oil.

3) In 5 ml of ethanol, 2.5 g of N-Boc-5-ethoxycarbonyl-1,2,3,6-tetrahydropyridine was dissolved, and 10 ml of a 1M aqueous solution of sodium hydroxide was added thereto. The reaction mixture was stirred for 4 hours at room temperature, and subsequently, a 5% aqueous solution of potassium hydrogensulfate was added thereto for acidification. The reaction mixture, was extracted with ethyl acetate. The extract was washed with saturated brine, and was subsequently dried over anhydrous sodium sulfate. After the desiccant was filtered off, the filtrate was concentrated under reduced pressure to yield crystals of crude 1-tert-butoxycarbonyl-1,2,3,6-tetrahydropyridine-5-carboxylic acid. The obtained crude 1-tert-butoxycarbonyl-1,2,3,6-tetrahydropyridine-5-carboxylic acid was dissolved in a mixed solution of 15 ml of chloroform and 2 ml of dimethylformamide, and subsequently, 1.6 g of 1-hydroxybenzotriazole hydrate and 2.0 g of 1-(3-dimethylaminopropyl)-3-ethylcarbodiimide hydrochloride were added thereto. The reaction mixture was stirred for 30 minutes at room temperature, and was subsequently ice-cooled. 28% aqueous ammonia in an amount of 0.64 ml was added thereto, and the reaction mixture was stirred for 1 hour. The reaction mixture was warmed up to room temperature, and subsequently concentrated under reduced pressure. A 5% aqueous solution of potassium hydrogencarbonate was poured thereinto. The reaction mixture was extracted with ethyl acetate. The extract was washed successively with a saturated aqueous solution of sodium hydrogen carbonate and saturated brine, and was then dried over anhydrous sodium sulfate. After the desiccant was filtered off, the filtrate was concentrated under reduced pressure. The residue was purified by silica gel column chromatography (eluent:hexane-ethyl acetate=1:2) to yield 1.4 g of 1-tert-butoxycarbonyl-5-carbamoyl-1,2,3,6-tetrahydropyridine as a crystal.

4) In 4.0 ml of chloroform, 1.1 g of 1-tert-butoxycarbonyl-5-carbamoyl-1,2,3,6-tetrahydropyridine was dissolved, and 4.0 ml of trifluoroacetic acid was added thereto. The reaction mixture was stirred for 30 minutes at room temperature, and was subsequently concentrated under reduced pressure to yield 1.4 g of crude 5-carbamoyl-1,2,3,6-tetrahydropyridine trifluoroacetate in the form of amorphous.

The crude 5-carbamoyl-1,2,3,6-tetrahydropyridine trifluoroacetate was dissolved in ethyl acetate, and hydrogen chloride was bubbled thereinto, followed by concentration under reduced pressure to yield crystals of 5-carbamoyl-1,2,3,6-tetrahydropyridine hydrochloride.

m.p. 270–272° C.

5-carbamoyl-1,2,3,6-tetrahydropyridine hydrochloride was dissolved in a saturated aqueous solution of sodium hydrogen carbonate, followed by extraction with chloroform. The organic layer was dried over anhydrous sodium sulfate. After the desiccant was filtered off, the filtrate was concentrated under reduced pressure to yield crystals of free 5-carbamoyl-1,2,3,6-tetrahydropyridine.

m.p. 122–124° C.

5) In 4 ml of ethanol, 0.27 g of 5-carbamoyl-1,2,3,6-tetrahydropyridine trifluoroacetate and 0.36 g of 4-chloro- 7-(4-isopropyl-2-methylthiophenyl)-2,5,6-trimethyl-7H-pyrrolo[2,3-d]pyrimidine were dissolved, and subsequently, 0.39 g of diisopropylethylamine was added thereto. The reaction mixture was heated under reflux for 8.5 hours, and subsequently, a saturated aqueous solution of sodium hydrogencarbonate was poured therein to. The reaction mixture was extracted with ethyl acetate. The extract was washed with saturated brine, and was then dried over anhydrous sodium sulfate. After the desiccant was filtered off, the filtrate was concentrated under reduced pressure. The residue was purified by silica gel column chromatography (eluent:chloroform—methanol=60:1), followed by crystallization from a mixed solvent of ethyl acetate-diethyl ether to yield 0.12 g of 4-(5-carbamoyl-1,2,3,6-tetrahydropyridin-1-yl)-7-(4-isopropyl-2-methylthiophenyl)-2,5,6-trimethyl-7H-pyrrolo[2,3-d]pyrimidine.

The structures and physical data of the present compound and of the compounds obtained in the same manner as described above are shown in Table 1.

EXAMPLE 3

Synthesis of 2-[6-(4-Carbamoyl-1,2,3,6-tetrahydropyridin-1-yl)-2-methyl-8-oxo-9-(4-isopropyl-2-methylthiophenyl)-8,9-dihydropurin-7-yl]-acetamide 1) In 5 ml of dimethylformamide, 0.70 g of 6-chloro-9-(4-isopropyl-2-methylthiophenyl)-2-methyl-8,9-dihydropurin-8-one was dissolved, and 80 mg of sodium hydride in an oil was added thereto with ice-cooling, followed by stirring for 40 minutes. Subsequently, 0.39 g of ethyl bromoacetate was added thereto, and the reaction mixture was warmed up to room temperature and was stirred for 20 minutes. Water was poured into the reaction mixture. The reaction mixture was extracted with ethyl acetate. The extract was washed with saturated brine, and was then dried over anhydrous sodium sulfate. After the desiccant was filtered off, the filtrate was concentrated under reduced pressure. The residue was purified by silica gel column chromatography (eluent:hexane-ethyl acetate=4:1) to yield 0.85 g of ethyl 2-[6-chloro-2-methyl-8-oxo-9-(4-isopropyl-2-methylthiophenyl)-8,9-dihydropurin-7-yl]acetate as an oil.

2) In a mixed solvent of 3 ml of methanol and 1 ml of water, 0.83 g of ethyl 2-[6-chloro-2-methyl-8-oxo-9-(4-isopropyl-2-methylthiophenyl)-8 9-dihydropurin-7-yl] acetate was dissolved, and subsequently, 80 mg of sodium hydroxide was added thereto. The reaction mixture was stirred for 30 minutes at room temperature. Water was poured into the reaction mixture. The reaction mixture was extracted with chloroform. The extract was dried over anhydrous sodium sulfate. After the desiccant was filtered off, the filtrate was concentrated under reduced pressure. The residue was purified by silica gel column chromatography (eluent:chloroform—methanol=8:1) to yield 0.47 g of 2-[6-chloro-2-methyl-8-oxo-9-(4-isopropyl-2-methylthiophenyl)-8,9-dihydropurin-7-yl]acetic acid as an oil.

3) In 4 ml of tetrahydrofuran, 0.47 g of 2-[6-chloro-2-methyl-8-oxo-9-(4-isopropyl-2-methylthiophenyl)-8,9-dihydropurin-7-yl]acetic acid was dissolved. After the reaction mixture was cooled to −15° C., 0.14 g of N-methylmorpholine and 0.19 g of isobutyl chloroformate was added thereto. After the reaction solution was stirred for 5 minutes, 0.085 ml of 28% aqueous ammonia was added thereto. The reaction mixture was warmed up to room temperature and was subsequently stirred overnight. Water was poured into the reaction mixture. The reaction mixture was extracted with ethyl acetate. The extract was dried over anhydrous sodium sulfate. After the desiccant was filtered off, the filtrate was concentrated under reduced pressure. The residue was purified by silica gel column chromatography (eluent:chloroform—methanol=50:1) to yield 0.41 g of 2-[6-chloro-2-methyl-8-oxo-9-(4-isopropyl-2-methylthiophenyl)-8,9-dihydropurin-7-yl]acetamide as an oil.

4) In 4 ml of ethanol, 0.16 g of 5-carbamoyl-1,2,3,6-tetrahydropyridine hydrochloride, 0.40 g of 2-[6-chloro-2-methyl-8-oxo-9-(4-isopropyl-2-methylthiophenyl)-8,9-dihydropurin-7-yl]acetamide, and 0.38 g of diisopropylethylamine were dissolved. Several drops of water were added thereto, and the reaction mixture was heated under reflux for 17 hours. The reaction mixture was concentrated under reduced pressure. The residue was purified by silica gel column chromatography (eluent:chloroform—methanol=7:1), followed by crystallization from ethyl acetate to yield 0.22 g of 2-[6-(4-carbamoyl-1,2,3,6-tetrahydropyridin-1-yl)-2-methyl-8-oxo-9-(4-isopropyl-2-methylthiophenyl)-8,9-dihydropurin-7-yl]acetamide.

The structures and physical data of the present compound and of the compounds obtained in the same manner as described above are shown in Table 1.

TABLE 1[*1]

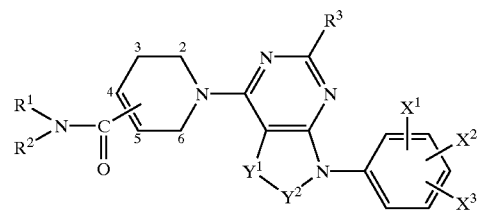

| Com. No. | Exp. No. | $R^1R^2$NCO | $Y^1$—$Y^2$ | $R^3$ | $X^1$ | $X^2$ | $X^3$ | m. p. (° C.) (Solvent for crystallization) |
|---|---|---|---|---|---|---|---|---|
| 01 | 1 | 4-H$_2$NCO | (Me)C═C(Me) | Me | 2-SMe | 4-i-Pr | H | 211–213 (AcOEt—Et$_2$O) |
| 02 | 1 | 4-H$_2$NCO | (Me)C═C(Me) | Me | 2-Br | 4-i-Pr | H | 224–226 (Hexane-AcOEt) |
| 03 | 1 | 4-H$_2$NCO | (Me)C═C(Me) | Me | 2-Me | 4-Me | 6-Me | 212–213 (Hexane-AcOEt) |
| 04 | 2 | 5-H$_2$NCO | (Me)C═C(Me) | Me | 2-SMe | 4-i-Pr | H | 147–149 (Et$_2$O) |
| 05 | 2 | 5-H$_2$NCO | (Me)C═C(Me) | Me | 2-Br | 4-i-Pr | H | 130–132 (Et$_2$O) |
| 06[*2] | 2 | 5-H$_2$NCO | (Me)C═C(Me) | Me | 2-Me | 4-Me | 6-Me | 189–192 (AcOEt) |

TABLE 1*1-continued

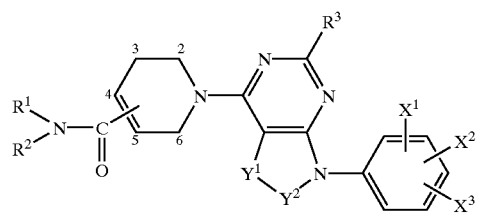

| Com. No. | Exp. No. | R¹R²NCO | Y¹—Y² | R³ | X¹ | X² | X³ | m. p. (° C.) (Solvent for crystallization) |
|---|---|---|---|---|---|---|---|---|
| 07 | 1 | 4-H₂NCO | (Me)C═C(H) | Me | 2-SMe | 4-i-Pr | H | 194–195 (AcOEt—Et₂O) |
| 08 | 1 | 4-H₂NCO | (Me)C═C(H) | Me | 2-Br | 4-i-Pr | H | 145–147 (Hexane-AcOEt) |
| 09 | 1 | 4-H₂NCO | (Me)C═C(H) | Me | 2-Me | 4-Me | 6-Me | 208–209 (Hexane-AcOEt) |
| 10 | 2 | 5-H₂NCO | (Me)C═C(H) | Me | 2-SMe | 4-i-Pr | H | 212–214 (Et₂O) |
| 11 | 2 | 5-H₂NCO | (Me)C═C(H) | Me | 2-Br | 4-i-Pr | H | 190–192 (Hexane-AcOEt) |
| 12 | 2 | 5-H₂NCO | (Me)C═C(H) | Me | 2-Me | 4-Me | 6-Me | 183–184 (Hexane-AcOEt) |
| 13 | 1 | 4-H₂NCO | (Et)C═C(Et) | Me | 2-Me | 4-Me | 6-Me | 157–159 (Hexane-AcOEt) |
| 14 | 2 | 5-H₂NCO | (Et)C═C(Et) | Me | 2-Me | 4-Me | 6-Me | 180–181 (Hexane-AcOEt) |
| 15 | 1 | 4-H₂NCO | (Et)C═N | Me | 2-Cl | 4-Cl | 6-Cl | 231–232 (Hexane-AcOEt) |
| 16 | 2 | 5-H₂NCO | (Et)C═N | Me | 2-Cl | 4-Cl | 6-Cl | 189–190 (Hexane-AcOEt) |
| 17 | 1 | 4-H₂NCO | (H)N—C(O) | Me | 2-SMe | 4-i-Pr | H | 202–204 (Et₂O) |
| 18 | 1 | 4-H₂NCO | (H)N—C(O) | Me | 2-Br | 4-i-Pr | H | 283–285 (Et₂O) |
| 19 | 1 | 4-H₂NCO | (H)N—C(O) | Me | 2-Me | 4-Me | 4-Me | 300–302 (Et₂O) |
| 20 | 2 | 5-H₂NCO | (H)N—C(O) | Me | 2-SMe | 4-i-Pr | H | 253–255 (Et₂O) |
| 21 | 2 | 5-H₂NCO | (H)N—C(O) | Me | 2-Br | 4-i-Pr | H | 205–207 (Et₂O) |
| 22 | 2 | 5-H₂NCO | (H)N—C(O) | Me | 2-Me | 4-Me | 4-Me | 257–259 (Et₂O) |
| 23 | 3 | 4-H₂NCO | (Me)N—C(O) | Me | 2-SMe | 4-i-Pr | H | 146–148 (Hexane-AcOEt) |
| 24 | 3 | 4-H₂NCO | (Me)N—C(O) | Me | 2-Br | 4-i-Pr | H | 211–213 (Hexane-AcOEt) |
| 25 | 3 | 4-H₂NCO | (Me)N—C(O) | Me | 2-Me | 4-Me | 4-Me | 224–226 (Hexane-AcOEt) |
| 26 | 3 | 5-H₂NCO | (Me)N—C(O) | Me | 2-SMe | 4-i-Pr | H | 179–181 (Et₂O) |
| 27 | 3 | 5-H₂NCO | (Me)N—C(O) | Me | 2-Br | 4-i-Pr | H | 210–211 (Et₂O) |
| 28 | 3 | 5-H₂NCO | (Me)N—C(O) | Me | 2-Me | 4-Me | 4-Me | 220–221 (Et₂O) |
| 29 | 3 | 4-H₂NCO | (Et)N—C(O) | Me | 2-SMe | 4-i-Pr | H | 209–211 (Hexane-AcOEt) |
| 30 | 3 | 4-H₂NCO | (Et)N—C(O) | Me | 2-Br | 4-i-Pr | H | 173–175 (Hexane-AcOEt) |
| 31 | 3 | 4-H₂NCO | (Et)N—C(O) | Me | 2-Me | 4-Me | 4-Me | 244–246 (Hexane-AcOEt) |
| 32 | 3 | 5-H₂NCO | (Et)N—C(O) | Me | 2-SMe | 4-i-Pr | H | 124–126 (Et₂O) |
| 33 | 3 | 5-H₂NCO | (Et)N—C(O) | Me | 2-Br | 4-i-Pr | H | 186–187 (Et₂O) |
| 34 | 3 | 5-H₂NCO | (Et)N—C(O) | Me | 2-Me | 4-Me | 4-Me | 207–209 (Et₂O) |
| 35 | 3 | 4-H₂NCO | (H₂NOCCH₃)N—C(O) | Me | 2-SMe | 4-i-Pr | H | 249–251 (AcOEt) |
| 36 | 1 | 4-H₂NCO | N═C(H) | Me | 2-SMe | 4-i-Pr | H | 145–147 (Et₂O) |
| 37 | 1 | 4-H₂NCO | N═C(CONH₂) | Me | 2-SMe | 4-i-Pr | H | 232–234 (Hexane-AcOEt) |
| 38 | 1 | 4-H₂NCO | N═N | Me | 2-SMe | 4-i-Pr | H | 198–199 (AcOEt—Et₂O) |
| 39 | 1 | 4-H₂NCO | (Me)C═C(Me) | Me | 2-Br | 4-Br | 6-Cl | 152–154 (Et₂O) |
| 40 | 1 | 4-H₂NCO | (Me)C═C(Me) | Me | 2-Cl | 4-Br | 6-Me | 158–160 (Et₂O) |
| 41 | 1 | 4-H₂NCO | (Me)C═C(Me) | Me | 2-Br | 4-Br | 6-Me | 157–159 (Et₂O) |
| 42 | 1 | 4-H₂NCO | (Me)C═C(Me) | Me | 2-Me | 4-Br | 6-Me | 166–168 (Et₂O) |
| 43 | 1 | 4-H₂NCO | (Me)C═C(Me) | Me | 2-Cl | 4-Cl | 6-Cl | 226–228 (Et₂O) |
| 44 | 1 | 4-H₂NCO | (Me)C═C(Me) | Me | 2-Br | 4-Br | 6-Br | 153–155 (Et₂O) |
| 45 | 1 | 4-H₂NCO | (Me)C═C(Me) | Me | 2-Cl | 4-OMe | 6-OMe | 143–145 (Et₂O) |
| 46 | 1 | 4-H₂NCO | (Me)C═C(Me) | Me | 2-Cl | 4-Br | 6-Cl | 146–148 (Hexane-AcOEt) |
| 47 | 1 | 4-H₂NCO | (Me)C═C(Me) | Me | 2-Br | 4-Br | 6-H | 245–247 (Hexane-AcOEt) |
| 48 | 1 | 4-H₂NCO | (Me)C═C(Me) | Me | 2-Cl | 4-Br | 6-H | 227–229 (Et₂O) |
| 49 | 1 | 4-H₂NCO | (Me)C═C(Me) | Me | 2-Br | 4-Cl | 6-H | 224–226 (Et₂O) |
| 50 | 1 | 4-H₂NCO | (Me)C═C(Me) | Me | 2-Br | 4-iPr | 6-Br | 156–158 (Hexane-AcOEt) |
| 51 | 1 | 4-H₂NCO | (Me)C═C(Me) | Me | 2-Br | 4-Br | 6-SMe | 161–163 (Hexane-AcOEt) |
| 52 | 1 | 4-H₂NCO | (Me)C═C(Me) | Me | 2-Br | 4-Br | 6-F | 145–147 (Hexane-AcOEt) |
| 53 | 1 | 4-H₂NCO | (Me)C═C(Me) | Me | 2-Br | 4-CF₃ | 6-Br | 229–231 (Hexane-AcOEt) |
| 54 | 1 | 4-MeHNCO | (Me)C═C(Me) | Me | 2-Br | 4-CF₃ | 6-Br | Amorphous*3 |
| 55 | 1 | 4-PrHNCO | (Me)C═C(Me) | Me | 2-Br | 4-CF₃ | 6-Br | Amorphous*4 |
| 56 | 1 | 4-PhHNCO | (Me)C═C(Me) | Me | 2-Br | 4-CF₃ | 6-Br | Amorphous*5 |
| 57 | 1 | 4-Me₂NCO | (Me)C═C(Me) | Me | 2-Br | 4-CF₃ | 6-Br | Amorphous*6 |
| 58 | 1 | 4-pyrrolidinoCO | (Me)C═C(Me) | Me | 2-Br | 4-CF₃ | 6-Br | Amorphous*7 |
| 59 | 1 | 4-morpholinoCO | (Me)C═C(Me) | Me | 2-Br | 4-CF₃ | 6-Br | Amorphous*8 |
| 60 | 1 | 4-H₂NCO | (Me)C═C(Me) | Me | 2-Me | 4-OMe | 6-Me | 217–219 (IPE) |
| 61 | 1 | 4-H₂NCO | (Me)C═C(Me) | Me | 2-Cl | 4-Cl | 6-Me | 141–143 (IPE) |
| 62 | 1 | 4-H₂NCO | (Me)C═C(Me) | Me | 2-Cl | 4-CF₃ | 6-Cl | 150–152 (IPE) |
| 63 | 1 | 4-H₂NCO | (Me)C═C(Me) | Me | 2-Br | 4-Br | 6-OMe | 176–178 (Et₂O) |
| 64 | 2 | 5-H₂NCO | (Me)C═C(Me) | Me | 2-Br | 4-Br | 6-Cl | 150–152 (Et₂O) |
| 65 | 2 | 5-H₂NCO | (Me)C═C(Me) | Me | 2-Cl | 4-Br | 6-Me | 143–145 (Et₂O) |
| 66 | 2 | 5-H₂NCO | (Me)C═C(Me) | Me | 2-Br | 4-Br | 6-Me | 144–146 (Et₂O) |
| 67 | 2 | 5-H₂NCO | (Me)C═C(Me) | Me | 2-Me | 4-Br | 6-Me | 138–140 (Et₂O) |
| 68 | 2 | 5-H₂NCO | (Me)C═C(Me) | Me | 2-Cl | 4-Cl | 6-Cl | 148–150 (Et₂O) |
| 69 | 2 | 5-H₂NCO | (Me)C═C(Me) | Me | 2-Br | 4-Br | 6-Br | 150–152 (Et₂O) |
| 70 | 2 | 5-H₂NCO | (Me)C═C(Me) | Me | 2-Cl | 4-OMe | 6-OMe | 145–147 (Et₂O) |
| 71 | 2 | 5-H₂NCO | (Me)C═C(Me) | Me | 2-Cl | 4-Br | 6-Cl | 148–150 (Hexane-AcOEt) |

TABLE 1-continued

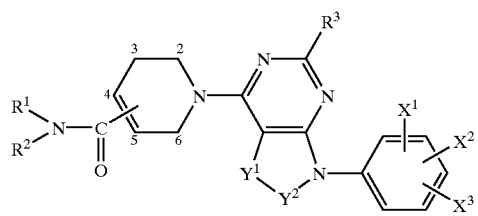

| Com. No. | Exp. No. | R¹R²NCO | Y¹—Y² | R³ | X¹ | X² | X³ | m. p. (° C.) (Solvent for crystallization) |
|---|---|---|---|---|---|---|---|---|
| 72 | 2 | 5-H₂NCO | (Me)C=C(Me) | Me | 2-Br | 4-Br | 6-H | 194–196 (Hexane-AcOEt) |
| 73 | 2 | 5-H₂NCO | (Me)C=C(Me) | Me | 2-Cl | 4-Br | 6-H | 165–167 (Et₂O) |
| 74 | 2 | 5-H₂NCO | (Me)C=C(Me) | Me | 2-Br | 4-Cl | 6-H | 187–189 (Et₂O) |
| 75 | 2 | 5-H₂NCO | (Me)C=C(Me) | Me | 2-Br | 4-iPr | 6-Br | 264–266 (Hexane-AcOEt) |
| 76 | 2 | 5-H₂NCO | (Me)C=C(Me) | Me | 2-Br | 4-Br | 6-SMe | 214–216 (Hexane-AcOEt) |
| 77 | 2 | 5-H₂NCO | (Me)C=C(Me) | Me | 2-Br | 4-Br | 6-F | 142–144 (Hexane-AcOEt) |
| 78 | 2 | 5-H₂NCO | (Me)C=C(Me) | Me | 2-Br | 4-CF₃ | 6-Br | 215–217 (Hexane-AcOEt) |
| 79 | 2 | 5-MeHNCO | (Me)C=C(Me) | Me | 2-Br | 4-CF₃ | 6-Br | Amorphous[*9] |
| 80 | 2 | 5-PrHNCO | (Me)C=C(Me) | Me | 2-Br | 4-CF₃ | 6-Br | Amorphous[*10] |
| 81 | 2 | 5-PhHNCO | (Me)C=C(Me) | Me | 2-Br | 4-CF₃ | 6-Br | Amorphous[*11] |
| 82 | 2 | 5-Me₂NCO | (Me)C=C(Me) | Me | 2-Br | 4-CF₃ | 6-Br | Amorphous[*12] |
| 83 | 2 | 5-pyrrolidinoCO | (Me)C=C(Me) | Me | 2-Br | 4-CF₃ | 6-Br | Amorphous[*13] |
| 84 | 2 | 5-morpholinoCO | (Me)C=C(Me) | Me | 2-Br | 4-CF₃ | 6-Br | Amorphous[*14] |
| 85 | 2 | 5-H₂NCO | (Me)C=C(Me) | Me | 2-Me | 4-OMe | 6-Me | Amorphous[*15] |
| 86 | 2 | 5-H₂NCO | (Me)C=C(Me) | Me | 2-Cl | 4-Cl | 6-Me | Amorphous[*16] |
| 87 | 2 | 5-H₂NCO | (Me)C=C(Me) | Me | 2-Cl | 4-CF₃ | 6-Cl | 216–218 (Et₂O) |
| 88 | 2 | 5-H₂NCO | (Me)C=C(Me) | Me | 2-Br | 4-Br | 6-OMe | 230–232 (Et₂O) |
| 89 | 1 | 4-H₂NCO | (Me)C=C(H) | Me | 2-Br | 4-Br | 6-Cl | 218–220 (AcOEt) |
| 90 | 1 | 4-H₂NCO | (Me)C=C(H) | Me | 2-Cl | 4-Br | 6-Me | 204–206 (AcOEt) |
| 91 | 1 | 4-H₂NCO | (Me)C=C(H) | Me | 2-Br | 4-Br | 6-Br | 248–250 (AcOEt) |
| 92 | 1 | 4-H₂NCO | (Me)C=C(H) | Me | 2-Br | 4-CF₃ | 6-Br | 235–237 (Et₂O) |
| 93 | 2 | 5-H₂NCO | (Me)C=C(H) | Me | 2-Br | 4-Br | 6-Cl | 282–284 (AcOEt) |
| 94 | 2 | 5-H₂NCO | (Me)C=C(H) | Me | 2-Cl | 4-Br | 6-Me | 255–257 (AcOEt/MeOH) |
| 95 | 2 | 5-H₂NCO | (Me)C=C(H) | Me | 2-Br | 4-Br | 6-Br | 287–289 (AcOEt) |
| 96 | 2 | 5-H₂NCO | (Me)C=C(H) | Me | 2-Br | 4-CF₃ | 6-Br | 253–255 (AcOEt) |
| 97 | 1 | 4-H₂NCO | (Me)C=C(Me) | Me | 2-Br | 4-CF₃ | 6-H | 242–243 (AcOEt) |
| 98 | 1 | 4-H₂NCO | (Me)C=C(Me) | Me | 2-Br | 4-NMe₂ | 6-H | 299–301 (AcOEt) |
| 99 | 1 | 4-H₂NCO | (Me)C=C(Me) | Me | 2-Cl | 4-CF₃ | 6-H | 232–234 (AcOEt) |
| 100 | 2 | 5-H₂NCO | (Me)C=C(Me) | Me | 2-Br | 4-CF₃ | 6-H | 239–240 (AcOEt) |
| 101 | 2 | 5-H₂NCO | (Me)C=C(Me) | Me | 2-Br | 4-NMe₂ | 6-H | 242–244 (AcOEt) |
| 102 | 2 | 5-H₂NCO | (Me)C=C(Me) | Me | 2-Cl | 4-CF₃ | 6-H | 233–235 (AcOEt) |
| 103 | 1 | 4-H₂NCO | (Me)C=C(H) | Me | 2-Me | 4-Br | 6-Me | 221–223 (AcOEt) |
| 104 | 1 | 4-H₂NCO | (Me)C=C(H) | Me | 2-SMe | 4-Br | 6-Br | 251–253 (Et₂O) |
| 105 | 1 | 4-H₂NCO | (Me)C=C(H) | Me | 2-Br | 4-CF₃ | 6-H | 230–231 (Et₂O) |
| 106 | 1 | 4-H₂NCO | (Me)C=C(H) | Me | 2-Br | 4-Br | 6-Me | 220–222 (AcOEt) |
| 107 | 1 | 4-H₂NCO | (Me)C=C(H) | Me | 2-OMe | 4-Br | 6-Br | 257–259 (Et₂O) |
| 108 | 1 | 4-H₂NCO | (Me)C=C(H) | Me | 2-Me | 4-Cl | 6-Cl | 180–182 (Et₂O) |
| 109 | 1 | 4-H₂NCO | (Me)C=C(H) | Me | 2-Cl | 4-Br | 6-Cl | 229–230 (Et₂O) |
| 110 | 1 | 4-H₂NCO | (Me)C=C(H) | Me | 2-Br | 4-Br | 6-H | 239–241 (Et₂O) |
| 111 | 1 | 4-H₂NCO | (Me)C=C(H) | Me | 2-Cl | 4-CF₃ | 6-H | 240–242 (Et₂O) |
| 112 | 1 | 4-H₂NCO | (Me)C=C(H) | Me | 2-Cl | 4-Br | 6-H | 237–239 (Et₂O) |
| 113 | 1 | 4-H₂NCO | (Me)C=C(H) | Me | 2-Br | 4-Cl | 6-H | 250–252 (Et₂O) |
| 114 | 1 | 4-H₂NCO | (Me)C=C(H) | Me | 2-Br | 4-NMe₂ | 6-H | 255–257 (Et₂O) |
| 115 | 2 | 5-H₂NCO | (Me)C=C(H) | Me | 2-Me | 4-Br | 6-Me | 232–234 (AcOEt) |
| 116 | 2 | 5-H₂NCO | (Me)C=C(H) | Me | 2-SMe | 4-Br | 6-Br | 168–170 (AcOEt) |
| 117 | 2 | 5-H₂NCO | (Me)C=C(H) | Me | 2-Br | 4-CF₃ | 6-H | 183–185 (Et₂O) |
| 118 | 2 | 5-H₂NCO | (Me)C=C(H) | Me | 2-Br | 4-Br | 6-Me | 260–262 (AcOEt) |
| 119 | 2 | 5-H₂NCO | (Me)C=C(H) | Me | 2-OMe | 4-Br | 6-Br | 233–235 (Et₂O) |
| 120 | 2 | 5-H₂NCO | (Me)C=C(H) | Me | 2-Me | 4-Cl | 6-Cl | 241–243 (Et₂O) |
| 121 | 2 | 5-H₂NCO | (Me)C=C(H) | Me | 2-Cl | 4-Br | 6-Cl | 284–285 (Et₂O) |
| 122 | 2 | 5-H₂NCO | (Me)C=C(H) | Me | 2-Br | 4-Br | 6-H | 227–228 (Et₂O) |
| 123 | 2 | 5-H₂NCO | (Me)C=C(H) | Me | 2-Cl | 4-CF₃ | 6-H | 200–202 (Et₂O) |
| 124 | 2 | 5-H₂NCO | (Me)C=C(H) | Me | 2-Cl | 4-Br | 6-H | 193–195 (Et₂O) |
| 125 | 2 | 5-H₂NCO | (Me)C=C(H) | Me | 2-Br | 4-Cl | 6-H | 223–225 (Et₂O) |
| 126 | 2 | 5-H₂NCO | (Me)C=C(H) | Me | 2-Br | 4-NMe₂ | 6-H | 197–199 (Et₂O) |
| 127 | 1 | 4-H₂NCO | (Me)C=C(Me) | Me | 2-Br | 4-Br | 6-OCF₃ | 142–144 (IPE) |
| 128 | 1 | 4-H₂NCO | (Me)C=C(Me) | Me | 2-Br | 4-OCF₃ | 6-Br | 212–214 (IPE) |
| 129 | 1 | 4-H₂NCO | (Me)C=C(H) | Me | 2-Br | 4-Br | 6-OCF₃ | 229–231 (AcOEt) |
| 130 | 1 | 4-H₂NCO | (Me)C=C(H) | Me | 2-Br | 4-OCF₃ | 6-Br | 233–235 (AcOEt) |
| 131 | 2 | 5-H₂NCO | (Me)C=C(Me) | Me | 2-Br | 4-Br | 6-OCF₃ | 128–130 (IPE) |
| 132 | 2 | 5-H₂NCO | (Me)C=C(Me) | Me | 2-Br | 4-OCF₃ | 6-Br | 231–233 (IPE) |
| 133 | 2 | 5-H₂NCO | (Me)C=C(H) | Me | 2-Br | 4-Br | 6-OCF₃ | 221–223 (AcOEt) |
| 134 | 2 | 5-H₂NCO | (Me)C=C(H) | Me | 2-Br | 4-OCF₃ | 6-Br | 254–256 (AcOEt) |

[*1](With regard to abbreviations in Table 1) Com. No. = Compound Number. Exp. No. = Example Number employed in synthesis. IPE = isopropyl ether.

TABLE 1*1-continued

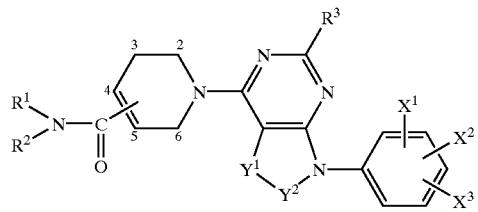

| Com. No. | Exp. No. | R¹R²NCO | Y¹—Y² | R³ | X¹ | X² | X³ | m. p. (° C.) (Solvent for crystallization) |
|---|---|---|---|---|---|---|---|---|

*²HCl salt
*³NMR (CDCl₃) δ (ppm); 2.05(3H, s), 2.40(3H, s), 2.49(3H, s), 2.56–2.72(2H, m), 2.91(3H, d, J=6.0Hz), 3.70(2H, t, J=5.2Hz), 4.13–4.26(2H, m), 5.70–5.88(1H, m), 6.62–6.73(1H, m), 7.95(2H, s).
ESIMS (Pos) m/z; 622(M+Na)⁺, 624(M+2+Na)⁺, 626(M+4+Na)⁺
*⁴NMR (CDCl₃) δ (ppm); 0.97(3H, t, J=7.5Hz), 1.50–1.64(2H, m), 2.05(3H, s), 2.40(3H, s), 2.49(3H, s), 2.56–2.73(2H, m), 3.32(2H, dd, J=13.6, 6.6Hz), 3.71(2H, t, J=5.5Hz), 4.12–4.27(2H, m), 5.70–5.83(1H, m), 6.60–6.72(1H, m), 7.95(2H, s).
ESIMS (Pos) m/z; 650(M+Na)⁺, 652(M+2+Na)⁺, 654(M+4+Na)⁺
*⁵NMR (CDCl₃) δ (ppm); 2.06(3H, s), 2.43(3H, s), 2.51(3H, s), 2.68–2.87(2H, m), 3.76(2H, t, J=5.4Hz), 4.20–4.35(2H, m), 6.72–6.88(1H, m), 7.06–7.63(6H, m), 7.40–7.58(1H, m), 7.95(2H, s).
ESIMS (Pos) m/z; 684(M+Na)⁺, 686(M+2+Na)⁺, 688(M+4+Na)⁺
*⁶NMR (CDCl₃) δ (ppm); 2.05(3H, s), 2.41(3H, s), 2.49(3H, s), 2.52–2.70(2H, m), 2.90–3.19(6H, m), 3.74(2H, t, J=5.5Hz), 4.06–4.20(2H, m), 5.91–6.02(1H, m), 7.95(2H, s).
ESIMS (Pos) m/z; 636(M+Na)⁺, 638(M+2+Na)⁺, 640(M+4+Na)⁺
*⁷NMR (CDCl₃) δ (ppm); 1.80–2.00(4H, m), 2.05(3H, s), 2.41(3H, s), 2.49(3H, s), 2.58–2.73(2H, m), 3.43–3.62(4H, m), 3.72(2H, t, J=5.4Hz), 4.09–4.20(2H, m), 6.07–6.17(1H, m), 7.96(1H, m).
ESIMS (Pos) m/z; 662(M+Na)⁺, 664(M+2+Na)⁺, 666(M+4+Na)⁺
*⁸NMR (CDCl₃) δ (ppm); 2.05(3H, s), 2.41(3H, s), 2.48(3H, s), 2.52–2.67(2H, m), 3.53–3.80(10H, m), 4.06–4.20(2H, m), 5.92–6.02(1H, m), 7.96(2H, s).
ESIMS (Pos) m/z; 678(M+Na)⁺, 680(M+2+Na)⁺, 682(M+4+Na)⁺
*⁹NMR (CDCl₃) δ (ppm); 2.04(3H, s), 2.41(3H, s), 2.49(3H, s), 2.45–2.60(2H, m), 2.91(3H, d, J=4.8Hz), 3.68(2H, t, J=5.6Hz), 4.25–4.35(2H, m), 5.78–5.92(1H, m), 6.60–6.70(1H, m), 7.95(2H, s).
ESIMS (Pos) m/z; 622(M+Na)⁺, 624(M+2+Na)⁺, 626(M+4+Na)⁺
*¹⁰NMR (CDCl₃) δ (ppm); 0.96(3H, t, J=7.5Hz), 1.50–1.66(2H, m), 2.03(3H, s), 2.41(3H, s), 2.49(3H, s), 2.42–2.60(2H, m), 3.31(2H, dd, J=13.9, 6.5Hz), 3.68(2H, t, J=5.6Hz), 4.25–4.35(2H, m), 5.72–5.87(1H, m), 6.58–6.68(1H, m), 7.95(2H, s).
ESIMS (Pos) m/z; 650(M+Na)⁺, 652(M+2+Na)⁺, 654(M+4+Na)⁺
*¹¹NMR (CDCl₃) δ (ppm); 2.04(3H, s), 2.43(3H, s), 2.50(3H, s), 2.54–2.67(2H, m), 3.75(2H, t, J=5.0Hz), 4.36–4.47(2H, m), 6.72–6.81(1H, m), 7.08–7.19(1H, m), 7.28–7.40(2H, m), 7.46–7.60(3H, m), 7.95(2H, s).
ESIMS (Pos) m/z; 684(M+Na)⁺, 686(M+2+Na)⁺, 688(M+4+Na)⁺
*¹²NMR (CDCl₃) δ (ppm); 2.04(3H, s), 2.41(3H, s), 2.47(3H, s), 2.28–2.52(2H, m), 2.83–3.20(6H, m), 3.72(2H, t, J=5.7Hz), 4.18–4.32(2H, m), 5.92–6.07(1H, m), 7.95(2H, s).
ESIMS (Pos) m/z; 636(M+Na)⁺, 638(M+2+Na)⁺, 640(M+4+Na)⁺
*¹³NMR (CDCl₃) δ (ppm); 1.75–2.02(4H, m), 2.03(3H, s), 2.41(3H, s), 2.47(3H, s), 2.35–2.55(2H, m), 3.45–3.65(4H, m), 3.72(2H, t, J=5.6Hz), 4.23–4.33(2H, m), 6.10–6.20(1H, m), 7.95(2H, s).
ESIMS (Pos) m/z; 662(M+Na)⁺, 664(M+2+Na)⁺, 666(M+4+Na)⁺
*¹⁴NMR (CDCl₃) δ (ppm); 2.05(3H, s), 2.41(3H, s), 2.46(3H, s), 2.31–2.50(2H, m), 3.69(8H, s), 3.62–3.77(2H, m), 4.20–4.30(2H, m), 5.96–6.07(1H, m), 7.96(2H, s).
ESIMS (Pos) m/z; 678(M+Na)⁺, 680(M+2+Na)⁺, 682(M+4+Na)⁺
*¹⁵NMR (CDCl₃) δ (ppm); 1.83(6H, s), 1.95(3H, s), 2.40(3H, s), 2.50(3H, s), 2.50–2.65(2H, m), 3.65(2H, t, J=6.0Hz), 3.83(3H, s), 4.25–4.32(2H, m), 5.63(2H, br s), 6.70(2H, s), 6.71–6.83(1H, m).
ESIMS (Pos) m/z; 420(M+H)⁺
*¹⁶NMR (CDCl₃) δ (ppm); 1.90(3H, s), 2.00(3H, s), 2.39(3H, s), 2.48(3H, s), 2.50–2.65(2H, m), 3.53–3.78(2H, m), 4.24–4.33(2H, m), 5.56(2H, br s), 6.72–6.82(1H, m), 7.26(1H, m), 7.42(1H, m).
ESIMS (Pos) m/z; 444(M+H)⁺

EXAMPLE 4

Synthesis of 2-Amino-4,5-dimethyl-1-(2,6-dibromo-4-trifluoromethylphenyl)pyrrole-3-carbonitrile In 15 ml of toluene, 5.5 g of 4-amino-3,5-dibromobenzotrifluoride, 1.9 g of acetoin, and 34 mg of p-toluenesulfonic acid were dissolved. The reaction solution was heated under reflux for 2.5 hours while conducting azeotropic dehydration. To the reaction mixture, 1.42 g of malononitrile was added. The reaction mixture was heated for 4 hours while being concentrated at 180° C. Water was added to the reaction mixture. The reaction mixture was extracted with chloroform, and subsequently, the extract was dried over anhydrous sodium sulfate. After the desiccant was filtered off, the filtrate was concentrated under reduced pressure. The residue was purified by silica gel column chromatography (eluent:hexane-ethyl acetate=5:1), and was allowed to stand for crystallization to yield 1.2 g of 2-amino-4,5-dimethyl-1-(2,6-dibromo-4-trifluoromethylphenyl) pyrrole-3-carbonitrile.

m.p. 158–161° C.

In the same manner as described above, the following compounds were synthesized.

2-Amino-4,5-dimethyl-1-(2,6-dibromo-4-isopropylphenyl) pyrrole-3-carbonitrile
m.p. 205–207° C.

2-Amino-4,5-dimethyl-1-(2,4,6-tribromophenyl)pyrrole-3-carbonitrile
m.p. 214–216° C.

2-Amino-4,5-dimethyl-1-(2,4-dibromo-6-chlorophenyl) pyrrole-3-carbonitrile
m.p. 206–208° C.

2-Amino-4,5-dimethyl-1-(2,4-dibromo-6-methylphenyl) pyrrole-3-carbonitrile
m.p. 186–189° C.

2-Amino-4,5-dimethyl-1-(2,4-dibromo-6-methylthiophenyl) pyrrole-3-carbonitrile
m.p. 136–138° C.

2-Amino-4,5-dimethyl-1-(2,4-dibromo-6-fluorophenyl) pyrrole-3-carbonitrile
m.p. 155–157° C.

2-Amino-4,5-dimethyl-1-(2,4-dibromo 6-methoxyphenyl) pyrrole-3-carbonitrile
NMR (CDCl$_3$) δ (ppm); 1.72 (3H, s), 2.07 (3H, s), 3.64 (2H, br s), 3.82 (3H, s), 7.15 (1H, d, J=2.0 Hz), 7.51 (1H, d, J=2.0 Hz);
ESIMS (Neg) m/z; 396 (M–H)$^-$, 398 (M+2–H)$^-$, 400 (M+4–H)$^-$.

2-Amino-4,5-dimethyl-1-(2,4-dibromo-6-trifluoromethoxyphenyl)pyrrole-3-carbonitrile
NMR (CDCl$_3$) δ (ppm); 1.75 (3H, s), 2.06 (3H, s), 3.33 (2H, br s), 7.56–7.63 (1H, m), 7.83–7.91 (1H, m).
ESIMS (Pos) m/z; 474 (M+Na)$^+$, 476 (M+2+Na)$^+$, 478 (M+4+Na)$^+$.

2-Amino-4,5-dimethyl-1-(2,6-dibromo-4-trifluoromethoxyphenyl)pyrrole-3-carbonitrile
NMR (CDCl$_3$) δ (ppm); 1.79 (3H, s), 2.19 (3H, s), 3 .65 (2H, br s), 7.61 (2H, S).
ESIMS (Pos) m/z; 474 (M+Na)$^+$, 476 (M+2+Na)$^+$, 478 (M+4+Na)$^+$.

2-Amino-4,5-dimethyl-7-(2,4-dibromo-6-trifluoromethylphenyl)pyrrole-3-carbonitrile
NMR (CDCl$_3$) δ (ppm); 1.74 (3H, s), 2.08 (3H, s), 3.55 (2H, br s), 7.95 (1H, d, J=2.0 Hz), 8.12 (1H, d, J=2.0 Hz).
ESIMS (Pos) m/z; 458 (M+Na)$^+$, 460 (M+2+Na)$^+$, 462 (M+4+Na)$^+$.

EXAMPLE 5

Synthesis of 4-Chloro-2,5,6-trimethyl-7-(2,6-dibromo-4-trifluoromethylphenyl )-7H-pyrrolo[2,3-d]pyrimidine 1) In 3 ml of acetic acid, 1.2 g of 2-amino-4,5-dimethyl-1-(2,6-dibromo-4-trifluoromethyl) pyrrole-3-carbonitrile and 0.82 g of acetic anhydride were dissolved. The reaction mixture was heated under reflux for 30 minutes. Subsequently, water was added thereto. The reaction mixture was extracted with ethyl acetate and was then dried over anhydrous sodium sulfate. After the desiccant was filtered off, the filtrate was concentrated to yield crude N-[3-cyano-4,5-dimethyl-1-(2,6-dibromo-4-trifluoromethylphenyl)-1H-pyrrol-2-yl]acetamide. To the obtained crude N-[3-cyano-4,5-dimethyl-1-(2,6-dibromo-4-trifluoromethylphenyl)-1H-pyrrol-2-yl]acetamide, 85% phosphoric acid in an amount of 3 ml was added, and the reaction mixture was heated for 0.5 hours at 130° C. Water was added to the reaction mixture. The reaction mixture was extracted with chloroform, and subsequently, the extract was dried over anhydrous sodium sulfate. After the desiccant was filtered off, the filtrate was concentrated under reduced pressure. The residue was purified by silica gel column chromatography (eluent:hexane-ethyl acetate=1:1) and was allowed to stand for crystallization to yield 0.67 g of 2,5,6-trimethyl-7-(2,6-dibromo-4-trifluoromethylphenyl)-3,7-dihydropyrrolo[2,3-d]pyrimidin-4-one.
NMR (CDCl$_3$) δ (ppm); 1.99 (3H, s), 2.43 (3H, s), 2.44 (3H, s), 7.96 (2H, d, J=0.7 Hz), 11.56 (1H, br s).
ESIMS (Neg) m/z; 476 (M–H)$^-$, 478 (M+2–H)$^-$, 480 (M+4–H)$^-$.

In the same manner as described above, the following compounds were synthesized.

2,5,6-trimethyl-7-(2,4-dibromo-6-chlorophenyl)-3,7-dihydropyrrolo[2,3-d]pyrimidin-4-one
NMR (DMSO-d$_6$) δ (ppm); 1.91 (3H, s), 2.20 (3H, s), 2.28 (3H, s), 8.10 (1H, d, J=2.2 Hz), 8.18 (1H, d, J=2.2 Hz), 11.80 (1H, br s).
ESIMS (Neg) m/z; 442 (M–H)$^-$, 444 (M+2–H)$^-$, 446 (M+4–H)$^-$.

2,5,6-Trimethyl-7-(2,4-dibromo-6-methylphenyl)-3,7-dihydropyrrolo[2,3-d]pyrimidin-4-one
NMR (DMSO-d$_6$) δ (ppm); 1.88 (3H, s), 1.90 (3H, s), 2.19 (3H, s), 2.29 (3H, s), 7.74 (1H, d, J=2.2 Hz), 7.95 (1H, d, J=2.2 Hz), 11.79 (1H, br s).
ESIMS (Neg) m/z;
422 (M–H)$^-$, 424 (M+2–H)$^-$, 426 (M+4–H)$^-$.

2,5,6-trimethyl-7-(2,4,6-tribromophenyl)-3,7-dihydropyrrolo [(2, 3-d]pyrimidin-4-one
NMR (DMSO-d$_6$) δ (ppm);
1.91 (3H, s), 2.20 (3H, S), 2.28 (3H, s), 8.20 (2H, s), 11.84 (1H, br s).
ESIMS (Neg) m/z; 486 (M–H)$^-$, 488 (M+2–H)$^-$, 490 (M+4–H)$^-$, 492 (M+6–H)$^-$.

2,5,6-Trimethyl-7-(2,4,6-dibromo-4-isopropylphenyl)-3,7-dihydropyrrolo[2,3-d]pyrimidin-4-one
NMR (CDCl$_3$) δ (ppm); 1.31 (6H, d, J=7.0 Hz), 1.98 (3H, s), 2.45 (6H, s), 2.95 (1H, Sept, J=7.0 Hz), 7.54 (2H, s), 12.18 (1H, br s).
ESIMS (Neg) m/z; 450 (M–H)$^-$, 452 (M+2–H)$^-$, 454 (M+4–H)$^-$.

2,5,6-trimethyl-7-(2,4-dibromo-6-methylthiophenyl)-3,7-dihydropyrrolo[2,3-d]pyrimidin-4-one
NMR (DMSO-d$_6$) δ (ppm); 1.88 (3H, s), 2.22 (3H, s), 2.28 (3H, s), 2.42 (3H, s), 7.51 (1H,d, J=2.0 Hz), 7.86 (1H, d, =2.0 Hz), 11.79 (1H, br s).
ESIMS (Neg) m/z; 454 (M–H)$^-$, 456 (M+2–H)$^-$, 458 (M+4–H)$^-$.

2,5,6-Trimethyl-7-(2,4-dibromo-6-fluorophenyl)-3,7-dihydropyrrolo[2,3-d]pyrimidin-4-one
NMR (DMSO-d$_6$) δ (ppm);
1.94 (3H, s), 2.20 (3H, s), 2.28 (3H, s), 7.97 (1H, dd, J=8.8, 1.9 Hz), 8.0 6 (1H, dd, J=3.5, 1.9 Hz), 11.86 (1H, br s).
ESIMS (Neg) m/z; 426 (M–H)$^-$, 428 (M+2–H)$^-$, 430 (M+4–H)$^-$.

2,5,6-Trimethyl-7-(2,4-dibromo-6-methoxyphenyl)-3,7-dihydropyrrolo[2,3-d]pyrimidin-4-one
NMR (DMSO-d$_6$) δ (ppm); 1.85 (3H, s), 2.18 (3H, s), 2.27 (3H, s), 3.76 (3H, s), 7.57 (1H, d, J=2.0 Hz) , 7. 66 (1H, d, J=2.0 Hz), 11.72 (1H, br s).
ESIMS (Neg) m/z; 438 (M–H)$^-$, 440 (M+2–H)$^-$, 442 (M+4–H)$^-$.

2,5,6-Trimethyl-7-(2,4-dibromo-6-trlifluoromethoxyphenyl)-3,7-dihydropyrrolo[2,3-d] pyrimidin-4-one
NMR (DMSO-d$_6$) δ (ppm); 1.92 (3H, s), 2.19 (3H, s), 2.28 (3H, s), 7.95–8.02 (1H, m), 8.23–8.30 (1H, m), 11.86 (1H, br s).
ESIMS (Neg) m/z; 492 (M–H)$^-$, 494 (M+2–H)$^-$, 496 (M+4 –H)$^-$.

2,5,6-Trimethyl-7-(2,6-dibromo-4-trifluoromethoxyphenyl)-3,7-dihydropyrrolo[2,3-d] pyrimidin-4-one
NMR (DMSO-d$_6$) δ (ppm); 1.90 (3H, s), 2.19 (3H, s), 2.28 (3H, s), 8.06 (2H, s), 11.85 (1H, br s)
ESIMS (Neg) m/z; 492 (M–H)$^-$, 494 (M+2–H)$^-$, 496 (M+4–H)$^-$.

2, Phosphorus oxychloride in an amount of 1.3 ml was added to 0.67 g of 2,5,6-trimethyl-7-(2,6-dibromo-4-trifluoromethylphenyl)-3,7-dihydropyrrolo[2,3-d] pyrimidin-4-one, and the reaction mixture was heated for 0.5 hours at 100° C. and was then cooled. The reaction mixture was poured into water with ice and was extracted with ethyl acetate. The organic layer was washed with a saturated aqueous solution of sodium hydrogencarbonate and was dried over anhydrous sodium sulfate. After the desiccant was filtered off, the filtrate was concentrated under reduced pressure and was allowed to stand for crystallization to yield 0.66 g of 4-chloro-2,5,6-trimethyl-7-(2,6-dibromo-4-trifluoromethylphenyl)-7H-pyrrolo[2,3-d]pyrimidine.

m.p. 202–204° C.

In the same manner as described above, the following compounds were synthesized.

4-Chloro-2,5,6-trimethyl-7-(2,6-dibromo-4-isopropylphenyl)-7H-pyrrolo[2,3-d]pyrimidine m.p. 173–175° C.

4-Chloro-2,5,6-trimethyl-7-(2,4,6-tribromophenyl)-7H-pyrrolo [2,3-d]pyrimidine m.p. 216–218° C.

4-Chloro-2,5,6-trimethyl-7-(2,4-dibromo-6-chlorophenyl)-7H-pyrrolo[2,3-d]pyrimidine m.p. 206–208° C.

4-Chloro-2,5,6-trimethyl-7-(2,4-dibriomo-6-methylphenyl)-7H-pyrrolo[2,3-d]pyrimidine m.p. 215–217° C.

4-Chloro-2,5,6-trimethyl-7-(2,4-dibromo-6-methylthiophenyl)-7H-pyrrolo[2,3-d]pyrimidine m.p. 249–251° C.

4-Chloro-2,5,6-trimethyl-7-(2,4-dibromo-6-fluorophenyl)-7H-pyrrolo[2,3-d]pyrimidine m.p. 170–172° C.

4-Chloro-2,5,6-trimethyl-7-(2,4-dibromo-6-methoxyphenyl)-7H-pyrrolo[2,3-d]pyrimidine NMR (CDCl$_3$) δ (ppm); 2.02 (3H, s), 2.41 (3H, s), 3.75 (3H, s), 7.57 (1H, d, J=2.0 Hz), 7.74 (1H, d, J =2.0 Hz)

ESIMS (Pos) m/z; 458 (M+H)$^+$, 460 (M+2+H)$^+$, 462 (M+4+H)$^+$.

4-chloro-2,5,6-trimethyl-7-(2,4-dibromo-6-trifluoromethoxyphenyl)-7H-pyrrolo[2,3-d]pyrimidine m.p. 148–150° C.

4-chloro-2,5,6-trimethyl-7-(2,6-dibromo-4-trifluoromethoxyphenyl)-7H-pyrrolo[2,3-d]pyrimidine m.p. 141–143° C.

EXAMPLE 6

Synthesis of 2-Amino-4-methyl-1-(2,4-dibromo-6-chlorophenyl) pyrrole-3-carbonitrile A mixture of 5.3 g of 6-chloro-2,4-dibromoaniline and 3.5 g of 2-(2-bromo-1-methylethylidene)malononitrile was dissolved in a mixed solution of 10 ml of isopropanol and 10 ml of tetrahydrofuran. The reaction mixture was heated for 2 hours while being concentrated at 120° C. Water was poured into the reaction mixture. The reaction mixture was extracted with chloroform. The organic layer was ;washed with a saturated aqueous solution of sodium hydrogencarbonate and was dried over anhydrous sodium sulfate. After the desiccant was filtered off, the filtrate was concentrated under reduced pressure and was allowed to stand for crystallization to yield 1.9 g of 2-amino-4-methyl-1-(2,4-dibromo-6-chlorophenyl)pyrrole-3-carbonitrile.

m.p. 197–199° C.

In the same manner as described above, the following compounds were synthesized.

2-Amino-4-methyl-1-(2,4,6-tribromophenyl)pyrrole-3-carbonitrile m.p. 208–210° C.

2-Amino-4-methyl-1-(2,4-dibromo-6-methylthiophenyl) pyrrole-3-carbonitrile m.p. 127–130° C.

2-Amino-4-methyl-1-(2,4-dibromo-6-methoxyphenyl) pyrrole-3-carbonitrile m.p. 122–125° C.

2-Amino-4-methyl-1-(2,6-dibromo-4-trifluoromethylphenyl) pyrrole-3-carbonitrile m.p. 178–180° C.

2-Amino-4-methyl-1-(2,4-dibromo-6-methylphenyl) pyrrole-3-carbonitrile m.p. 169–171° C.

2-Amino-4-methyl-1-(2,4-dibromo-6-trifluoromethoxyphenyl) pyrrole-3-carbonitrile m.p. 158–160° C.

2-Amino-4-methyl-1-(2,6-dibromo-4-trifluoromethoxyphenyl) pyrrole-3-carbonitrile NMR (CDCl$_3$) δ (ppm); 2.16 (3H, d, J=1.1 Hz), 3.76 (2H, br s), 5.87 (1H, d, J=1.1 Hz), 7.58 (2H, d, J=0.8 Hz).

ESIMS (Neg) m/z; 436 (M–H)$^-$, 438 (M+2–H)$^-$, 440 (M+4–H)$^-$.

2-Amino-4-methyl-1-(2,4-dibromo-6-trifluoromethylphenyl)pyrrole-3-carbonitrile

NMR (CDCl$_3$) δ (ppm); 2.12 (3H, s), 3.66 (2H, br s), 5.87 (1H, s), 7.92 (1H, d, J=2.0 Hz), 8.10 (1H, d, J=2.0 Hz)

ESIMS (Pos) m/z; 444 (M+Na)$^+$, 446 (M+2+Na)$^+$, 448 (M+4+Na)$^+$.

EXAMPLE 7

Synthesis of 4-Chloro-2,5-dimethyl-7-(2,4-dibromo-6-chlorophenyl)-7H-pyrrolo[2,3-d]pyrimidine 1) In 5 ml of acetic acid, 1.9 g of 2-Amino-4-methyl-1-(2,4-dibromo-6-chlorophenyl)pyrrole-3-carbonitrile and 1.48 g of acetic anhydride were dissolved. The reaction mixture was heated under reflux for 30 minutes. Water was added to the reaction mixture, and the reaction mixture was extracted with ethyl acetate. Subsequently, the extract was dried over anhydrous sodium sulfate. After the desiccant was filtered off, the filtrate was concentrated under reduced pressure to yield crude N-[3-cyano-4-methyl-1-(2,4-dibromo-6-chlorophenyl)-1H-pyrrol-2-yl]acetamide. To the obtained crude N-[3-cyano-4-methyl-1-(2,4-dibromo-6-chlorophenyl)-1H-pyrrol-2-yl]acetamide, 8ml of 85% phosphoric acid were added. The reaction mixture was heated for 0.5 hours at 130° C., and subsequently, water was added thereto. The reaction mixture was extracted with chloroform, and subsequently, the extract was dried over anhydrous sodium sulfate. After the desiccant was filtered off, the filtrate was concentrated under reduced pressure. The residue was purified by silica gel column chromatography (eluent:hexane ethyl acetate=1:1) and was allowed to stand for crystallization. The precipitated crystals were washed with ethyl acetate to yield 1.1 g of 2,5-dimethyl-7-(2,4-dibromo-6-chlorophenyl)-3,7-dihydropyrrolo[2,3-d]pyrimidin -4-one.

NMR (CDCl$_3$) δ (ppm); 2.22 (3H, s), 2.31 (3H, d, J=1.1 Hz), 6.80 (1H, d, J=1.1 Hz), 8.06 (1H, d, J=2.11 Hz), 8.14 (1H, d, J 2.1 Hz), 11.91 (1H, br s).

ESIMS (Neg) m/z; 428 (M–H)$^-$, 430 (M+2–H)$^-$, 432 (M+4–H)$^-$.

In the same manner as described above, the following compounds were synthesized.

2,5-Dimethyl-7-(2,4-dibromo-6-methylphenyl)-3,7-dihydropyrrolo[2,3-d]pyrimidin-4-one.

NMR (DMSO-d$_6$) δ (ppm); 1.96 (3H, s), 2.21 (3H, s), 2.32 (3H, d, J=1.1 Hz), 6.75 (1H, d, J=1.1 Hz), 7.70 (1H, d, J=2.1 Hz), 7.91 (1H, d, J=2.1 Hz), 11.86 (1H, br s).

ESIMS (Neg) m/z; 408 (M−H)⁻, 410 (M+2−H)⁻, 412 (M+4−H)⁻.

2,5-Dimethyl-7-(2,4,6-tribromophenyl)-3,7-dihydropyrrolo[2,3-d]pyrimidin-4-one.

NMR (DMSO-d$_6$) δ (ppm); 2.23 (3H, s), 2.31 (3H, d, J=1.1 Hz), 6.78 (1H, d, J=1.1 Hz), 8.16 (2H, s), 11.90 (1H, br s).

ESIMS (Neg) m/z; 472(M−H)⁻, 474 (M+2−H)⁻, 476 (M+4−H)⁻, 478 (M+6−H)⁻.

2,5-Dimethyl-7-(2,4-dibromo-6-methylthiophenyl)-3,7-dihydropyrrolo[2,3-d]pyrimidin-4-one.

NMR (DMSO-d$_6$) δ (ppm); 2.21(3H, s), 2.31 (3H, d, J=1.1 Hz), 2.41 (3H, s), 6.67 (1H, d, J=1.1 Hz), 7.50 (1H, d, J=2.1 Hz), 7.83 (1H, d, J=2.1 Hz), 11.86 (1H, br s).

ESIMS (Neg) m/z; 440 (M−H)⁻, 442 (M+2−H)⁻, 444 (M+4−H)⁻.

2,5-Dimethyl-7-(2,6-dibromo-4-trifluoromethylphenyl)-3,7-dihydropyrrolo[2,3-d]pyrimidin-4-one.

NMR (DMSO-d$_6$) δ (ppm); 2.22 (3H, s), 2.33 (3H, d, J=1.2 Hz), 6.84 (1H, d, J=1.2 Hz), 8.31 (2H, d, J=0.6 Hz), 11.94 (1H, br s).

ESIMS (Neg) m/z; 462 (M−H)⁻, 464 (M+2−H)⁻, 466 (M+4−H)⁻.

2,5-Dimethyl-7-(2,4-dibromo-6-methoxyphenyl)-3,7-dihydropyrrolo[2,3-d]pyrimidin-4-one.

NMR (DMSO-d$_6$) δ (ppm); 2.20 (3H, s), 2.29 (3H, d, J=1.1 Hz), 3.74 (3H, s), 6.66 (1H, d, J=1.1 Hz), 7.47 (1H, d, J=2.0 Hz), 7.62 (1H, d, J=2.0 Hz), 11.79 (1H, br s).

ESIMS (Neg) m/z; 424 (M−H)⁻, 426 (M+2−H)⁻, 428 (M+4−H)⁻.

2,5-Dimethyl-7-(2,4-dibromo-6-trifluoromethoxyphenyl)-3,7-dihydropyrrolo[2,3-d]pyrimidin-4-one.

NMR (CDCl$_3$) δ (ppm); 2.41 (3H, s), 2.47 (3H, s), 6.48 (1H, s), 7.51–7.58 (1H, m), 7.82–7.87 (1H, m), 10.64 (1H, br s).

ESIMS (Neg) m/z; 478 (M−H)⁻, 480 (M+2−H)⁻, 482 (M+4−H)⁻.

2,5-Dimethyl-7-(2,6-dibromo-4-trifluoromethoxyphenyl)-3,7-dihydropyrrolo[2,3-d]pyrimidin-4-one.

NMR (CDCl$_3$) δ (ppm); 2.43 (3H, s), 2.48 (3H, s), 6.47 (1H, s), 7.57 (2H, s), 10.62 (1H, br s).

ESIMS (Neg) m/z; 478 (M−H)⁻, 480 (M+2−H)⁻, 482 (M+4−H)⁻.

2) To 1.0 g of 2,5-dimethyl-7-(2,4-dibromo-6-chlorophenyl)-3,7-dihydropyrrolo[2,3-d]pyrimidin-4-one, 3.2 ml of phosphorus oxychloride was added. The reaction mixture was heated for 0.5 hours at 100° C. and was then cooled. The reaction mixture was poured into water with ice and was subsequently extracted with ethyl acetate. The organic layer was washed with a saturated aqueous solution of sodium hydrogencarbonate and was dried over anhydrous sodium sulfate. After the desiccant was filtered off, the filtrate was concentrated under reduced pressure and was then allowed to stand for crystallization. The precipitated crystals were washed with hexane-ether to yield 0.76 g of 4-Chloro-2,5-dimethyl-7-(2,4-dibromo-6-chlorophenyl)-7H-pyrrolo[2,3-d]pyrimidine.

m.p. 157–159° C.

In the same manner as described above, the following compounds were synthesized.

4-Chloro-2,5-dimethyl-7-(2,4,6-tribromophenyl)-7H-pyrrolo[2,3-d]pyrimidine m.p. 162–164° C.

4-Chloro-2,5-dimethyl-7-(2,4-dibromo-6-methylthiophenyl)-7H-pyrrolo[2,3-d]pyrimidine m.p. 203–205° C.

4-Chloro-2,5-dimethyl-7-(2,4-dibromo-6-methoxyphenyl)-7H-pyrrolo[2,3-d]pyrimidine m.p. 175–177° C.

4-Chloro-2,5-dimethyl-7-(2,6-dibromo-4-trifluoromethylphenyl)-7H-pyrrolo[2,3-d]pyrimidine m.p. 153–155° C.

4-Chloro-2,5-dimethyl-7-(2,4-dibromo-6-methylphenyl)-7H-pyrrolo[2,3-d]pyrimidine m.p. 159–161° C.

4-Chloro-2,5-dimethyl-7-(2,4-dibromo-6-trifluoromethoxyphenyl)-7H-pyrrolo.[2,3-d]pyrimidine m.p. 157–159° C.

4-Chloro-2,5-dimethyl-7-(2,6-dibromo-4-trifluoromethoxyphenyl)-7H-pyrrolo[2,3-d]pyrimidine NMR (CDCl$_3$) δ (ppm); 2.54 (3H, d, J=1.1 Hz), 2.68 (3H, s), 6.82 (1H, d, J=1.1 Hz), 7.60 (2H, d, J=0.9 Hz).

ESIMS (Pos) m/z; 498 (M+H)⁺, 500 (M+2+H)⁺, 502 (M+4+H)+, 504 (M+6+H)⁺.

EXPERIMENTAL EXAMPLE

CRF Receptor Binding Experiment

As a receptor preparation, the frontal cortex membranes of rats were employed.

As a $^{125}$I labeled ligand, $^{125}$I-CRF was employed.

The binding reaction employing a $^{125}$I labeled ligand was carried out in the following method as described in The Journal of Neuroscience, 7, 88 (1987).

Preparation of the receptor membrane preparations: The frontal cortex of rats was homogenized in a 50 mM Tris hydrochloric acid buffer (pH 7.0) containing 10 mM MgCl$_2$ and 2 mM EDTA, and subsequently, the homogenized mixture was centrifuged at 48,000×g. The precipitate was washed once with the Tris hydrochloric acid buffer. The precipitate was suspended in a 50 mM tris hydrochloric acid buffer (pH 7.0) containing 10 mM MgCl$_2$, 2 mM EDTA, 0.1% bovine serum albumin, and 100 kalliklein unit/ml aprotinin, to produce a membrane preparation.

CRF receptor binding experiment: The membrane preparation (0.3 mg protein/ml), $^{125}$I-CRF (0.2 nM), and a test agent were reacted for 2 hours at 25° C. After completion of the reaction, the reaction mixture was filtered with suction using a glass filter (GF/C) treated with 0.3% polyethyleneimine, and the glass filter was washed three times with a phosphoric-acid-buffered physiological saline solution containing 0.01% Triton X-100. After completion of the washing, the radioactivity of the filter paper was measured by a gamma counter.

The binding quantity obtained when the reaction was carried out in the presence of 1 μM CRF was determined as nonspecific binding of $^{125}$I-CRF, while the difference between the total binding and the nonspecific binding was determined as a specific binding. A control curve was obtained by reacting $^{125}$I-CRF with a constant concentration and a test agent whose concentrations were varied, under the conditions described above. From the control curve, the concentration of the test agent for controlling 50% of the binding of $^{125}$I-CRF (IC$_{50}$) was determined.

As a result, the representative compounds indicating the IC$_{50}$ values of 100 nM or lower were the following compounds of Com. Nos. in Table 1.

Com. Nos.: 01, 02, 07, 12, 39, 44, 46, 47, 51, 53, 61, 63, 66, 69, 72, 78, 79, 87, 88, 89, 913, 97, 104, 107, 116, and 118.

Industrial Applicability

According to the present invention, the compounds exhibiting high affinity for CRF receptors have been provided.

These compounds are effective for diseases which are believed to involve CRF, such as depression, anxiety, Alzheimer's disease, Parkinson's disease, Huntington's chorea, eating disorders, hypertension, digestive tract diseases, drug dependence, epilepsy, cerebral infarction, cerebral ischemia, cerebral edema, head trauma, inflammation, and immune system-related diseases.

What is claimed is:

1. A carbamoyl tetrahydropyridine derivative represented by the formula:

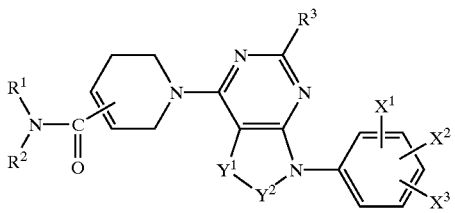

wherein: $R^1$ and $R^2$ are identical or different, and each represents a hydrogen atom, a $C_1$–$C_5$ alkyl group, or a phenyl group, or alternatively, $R^1$ and $R^2$, taken together with the nitrogen atom to consisting of a pyrrolidino group, a piperidino group, a morpholino group, a thiomorpholino group, a piperazino group, and a 4-methylpiperazino group; $R^3$ represents a hydrogen atom or a $C_1$–$C_5$ alkyl group; $Y^1$–$Y^2$ represents $(R^4)C=C(R^5)$, $(R^6)C=N$, $N=N$, $(R^7)N$—CO, or $N=C(R^8)$; $X^1$, $X^2$, and $X^3$ are identical or different, and each represents a hydrogen atom, a halogen atom, a $C_1$–$C_5$ alkyl group, a $C_1$–$C_5$ alkoxy group, a $C_1$–$C_5$ alkylthio group, a trifluoromethyl group, a trifluoromethoxy group, an amino group, or a $C_1$–$C_5$ alkylamino group; wherein $R^4$ and $R^5$ are identical or different, and each represents a hydrogen atom or a $C_1$–$C_5$ alkyl group; $R^6$ represents a hydrogen atom or a $C_1$–$C_5$ alkyl group; $R^7$ represents a hydrogen atom, a $C_1$–$C_5$ alkyl group, a ($C_1$–$C_5$ alkoxy)carbonylmethyl group, a carboxymethyl group, or a group represented by the formula: $CH_2CONR^{11}(R^{12})$, wherein $R^{11}$ and $R^{12}$ are identical or different, and each represents a hydrogen atom or a $C_1$–$C_5$ alkyl group, or alternatively, $R^{11}$ and $R^{12}$, taken together with the nitrogen atom to which they are adjacent, represent a saturated heterocyclic group selected from the group consisting of a pyrrolidino group, a piperidino group, a morpholino group, a thiomorpholino group, a piperazino group, and a 4-methylpiperazino group; and $R^8$ represents a hydrogen atom or a carbamoyl group; or a pharmaceutically acceptable salt thereof.

2. The carbamoyl tetrahydropyridine derivative or the pharmaceutically acceptable salt thereof, according to claim 1, wherein $R^1$ and $R^2$ each represent a hydrogen atom.

3. The carbamoyl tetrahydropyridine derivative or the pharmaceutically acceptable salt thereof, according to claim 2, wherein $R^3$ represents a methyl group; $Y^1$–$Y^2$ represents $(R^4)C=C(R^5)$; and $R^4$ and $R^5$ are identical or different, and each represents a hydrogen atom or a methyl group.

4. A pyrrolopyrimidine derivative represented by the formula:

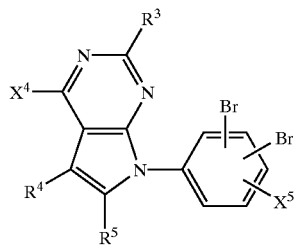

wherein $R^3$ represents a hydrogen atom or a $C_1$–$C_5$ alkyl group; $R^4$ and $R^5$ are identical or different, and each represents a hydrogen atom or a $C_1$–$C_5$ alkyl group; $X^4$ represents a hydroxyl group, a chlorine atom, a bromine atom, or an iodine atom; and $X^5$ represents a halogen atom, a $C_1$–$C_5$ alkyl group, a $C_1$–$C_5$ alkoxy group, a $C_{1-C_5}$ alkylthio group, a trifluoromethyl group, or a trifluoromethoxy group.

5. The carbamoyl tetrahydropyridine derivative or the pharmaceutically acceptable salt thereof, according to claim 1, wherein $R^1$ and $R^2$, taken together with the nitrogen atom to which they are adjacent, form said saturated heterocyclic group.

6. The carbamoyl tetrahydropyridine derivative or the pharmaceutically acceptable salt thereof, according to claim 1, wherein $R^{11}$ and $R^{12}$, taken together with the nitrogen atom to which they are adjacent, form said saturated heterocyclic group.

7. The carbamoyl tetrahydropyridine derivative or the pharmaceutically acceptable salt thereof, according to claim 1, wherein $R^1$ and $R^2$, taken together with the nitrogen atom to which they are adjacent, form said saturated heterocyclic group; and wherein $R^{11}$ and $R^{12}$, taken together with the nitrogen atom to which they are adjacent, form said saturated heterocyclic group.

* * * * *

UNITED STATES PATENT AND TRADEMARK OFFICE
CERTIFICATE OF CORRECTION

PATENT NO. : 6,600,038 B1
DATED : July 29, 2003
INVENTOR(S) : Nakazato et al.

It is certified that error appears in the above-identified patent and that said Letters Patent is hereby corrected as shown below:

Column 4,
Line 56, "tartearic" should read -- tartaric --.

Column 10,
Line 44, "4-carbamoyl-1,12,3,6-" should read -- "4-carbamoyl-1,2,3,6- --.

Column 11,
Line 38, "≤" should read -- = --.
Line 61, "ethoxycarbohylpiperidin" should read -- ethoxycarbonylpiperidin --; and
Line 63, "ethoxycarnonylpiperidin" should read -- ethoxycarbonylpiperidin --.

Column 13,
Line 3, "diisopiopylethylamine" should read -- diisopropylethylamine --.

Column 19,
Line 9, under the formula, "7.06-7.63(6H, m)" should read -- "7.06-7.63(5H, m) --.

Column 21,
Line 22, "2-Amino-4,5-dimethyl-7-(2,4,-dibromo-6-" should read
-- 2-Amino-4,5-dimethyl-1-(2,4,-dibromo-6- --.

Column 24,
Line 56, "J=2.11 Hz)," should read -- "J-2.1 Hz), --.

Column 26,
Line 62, "913" should read -- 93 --.

Column 27,
Line 23, after "atom to" insert -- which they are adjacent, represent a saturated heterocyclic group selected from the group --.

UNITED STATES PATENT AND TRADEMARK OFFICE
CERTIFICATE OF CORRECTION

PATENT NO.    : 6,600,038 B1
DATED         : July 29, 2003
INVENTOR(S)   : Nakazato et al.

It is certified that error appears in the above-identified patent and that said Letters Patent is hereby corrected as shown below:

Column 28,
Line 27, "$C_{1-C5}$" should read -- $C_1$-$C_5$ --.

Signed and Sealed this

Eleventh Day of May, 2004

JON W. DUDAS
*Acting Director of the United States Patent and Trademark Office*